(12) United States Patent
Xu et al.

(10) Patent No.: US 10,054,594 B2
(45) Date of Patent: Aug. 21, 2018

(54) PROCESSING, MODEL ESTABLISHMENT, AND PREDICATION METHODS OF MULTI-POSITION DIFFUSE SPECTRAL DATA AND PROCESSING APPARATUS

(71) Applicant: Tianjin Sunrise Technologies Development Co., Ltd., Tianjin (CN)

(72) Inventors: Kexin Xu, Tianjin (CN); Jin Liu, Tianjin (CN); Wanjie Zhang, Tianjin (CN)

(73) Assignee: Tianjin Sunrise Technologies Development Co., Ltd., Tianjin (CN)

( * ) Notice: Subject to any disclaimer, the term of this patent is extended or adjusted under 35 U.S.C. 154(b) by 236 days.

(21) Appl. No.: 14/863,078

(22) Filed: Sep. 23, 2015

(65) Prior Publication Data

US 2016/0091496 A1    Mar. 31, 2016

(30) Foreign Application Priority Data

Sep. 28, 2014 (CN) .......................... 2014 1 0508057

(51) Int. Cl.
*G01N 33/66* (2006.01)
*G02B 6/04* (2006.01)
(Continued)

(52) U.S. Cl.
CPC ........... *G01N 33/66* (2013.01); *A61B 5/0075* (2013.01); *A61B 5/1455* (2013.01); *A61B 5/14532* (2013.01); *A61B 5/7203* (2013.01); *A61B 5/7239* (2013.01); *G01J 3/00* (2013.01); *G01N 21/474* (2013.01); *G01N 21/49* (2013.01);
(Continued)

(58) Field of Classification Search
CPC ..................................................... G01N 33/66
See application file for complete search history.

(56) References Cited

U.S. PATENT DOCUMENTS

| | | | |
|---|---|---|---|
| 2002/0084417 A1 | 7/2002 | Khalil et al. | |
| 2005/0002031 A1 | 1/2005 | Kraemer et al. | |
| | (Continued) | | |

FOREIGN PATENT DOCUMENTS

| | | |
|---|---|---|
| CN | 1699973 | 11/2005 |
| CN | 1699973 A | 11/2005 |
| | (Continued) | |

OTHER PUBLICATIONS

Maruo, K., et al., "Noninvasive Blood Glucose Assay Using a Newly Developed Near-Infrared System," IEEE Journal of Selected Topics in Quantum Electronics, 2003, vol. 9, No. 2, Mar./Apr. 2003, pp. 322-330.

(Continued)

*Primary Examiner* — Hugh H Maupin
(74) *Attorney, Agent, or Firm* — McDermott Will & Emery LLP

(57) ABSTRACT

A method of processing spectral data is disclosed and may include the steps of illuminating a medium to detect an inside particular component with light; obtaining a first spectral data for the medium at a first radial position and a second spectral data for the medium at a second radial position, wherein the first radial position and the second radial position are selected arbitrarily; and performing differential processing on the first spectral data and the second spectral data.

23 Claims, 17 Drawing Sheets

(51) Int. Cl.
    *G01N 21/49*     (2006.01)
    *G02B 6/36*     (2006.01)
    *G01N 21/47*     (2006.01)
    *A61B 5/00*     (2006.01)
    *A61B 5/145*     (2006.01)
    *A61B 5/1455*     (2006.01)
    *G01J 3/00*     (2006.01)

(52) U.S. Cl.
    CPC ............ G02B 6/04 (2013.01); G02B 6/3624 (2013.01); *A61B 2562/0238* (2013.01); *G01N 2021/4747* (2013.01)

(56) References Cited

U.S. PATENT DOCUMENTS

| | | |
|---|---|---|
| 2006/0063995 A1 | 3/2006 | Yodh et al. |
| 2016/0097716 A1* | 4/2016 | Gulati ................ A61B 5/02416 250/339.01 |
| 2016/0242682 A1* | 8/2016 | Gulati ................ A61B 5/1455 |

FOREIGN PATENT DOCUMENTS

| | | | |
|---|---|---|---|
| JP | 2007007267 A | * | 1/2007 |
| WO | WO 2007/004604 A1 | | 1/2007 |

OTHER PUBLICATIONS

Maruo, K., et al., "New Methodology to Obtain a Calibration Model for Noninvasive Near-Infrared Blood Glucose Monitoring," Applied Spectroscopy, vol. 60, No. 4, 2006, pp. 441-449.

Jensen, Peter Snoer, et al., "Influence of Temperature on Water and Aqueous Glucose Absorption Spectra in the Near- and Mid-Infrared Regions at Physiologically Relevant Temperatures," vol. 57, No. 1, 2003, pp. 28-36.

Laufer, Jan, et al., "Effect of Temperature on the Optical Properties of Ex Vivo Human Dermis and Subdermis," Phys. Med. Biol., vol. 43, 1998, pp. 2479-2489.

Troy, Tamara L., et al., "Optical Properties of Human Skin in the Near Infrared Wavelength Range of 1000 to 2200 nm," Journal of Biomedical Optical, 6(2), Apr. 2001, pp. 167-176.

Chinese Office Action issued in corresponding Chinese priority application 201410508057.2 dated Nov. 27, 2017 (6 pages).

* cited by examiner

PROCESSING, MODEL ESTABLISHMENT, AND PREDICATION METHODS OF MULTI-POSITION DIFFUSE SPECTRAL DATA AND PROCESSING APPARATUS

CROSS-REFERENCE TO RELATED APPLICATION(S)

This application claims priority to Chinese Application No. 201410508057.2, filed on Sep. 28, 2014, which is incorporated herein by reference in its entirety.

TECHNICAL FIELD

The present disclosure generally relates to the field of spectroscopy, and more particularly, to a spectroscopy method, a method of model establishment and a prediction method for component concentration, and a processing apparatus for spectroscopy.

BACKGROUND

The spectroscopy technology has various advantages, such as environmental benefits, pollution-free, no damages to samples, fast detection speed, simultaneous quantitative analyses of multiple components, no need for any reagents or test paper, continuous and real-time monitoring, or the like. It is a real nondestructive detection technique. In the biomedical field, near-infrared spectroscopy has been employed to realize rapid and non-invasive detection of biochemical parameters such as degree of blood oxygen saturation. Near-infrared spectroscopy is considered as one of the most promising non-invasive techniques for some chemical components' detection in human bodies.

In component concentration detection by spectroscopy, substances to be detected are usually complex samples without being subjected to pre-processing such as refinement, or certain substances in a human body. The concentration of a component can be determined by establishing a prediction model using a multi-variable regression method when the component have obvious absorption characteristic on a given waveband. However, there may be many unpredictable interferential factors in the complex samples or bodies. For example, the absorption spectrum of some components in the human body may be seriously influenced by body temperature or mood and thus do not have obvious absorption characteristics on the given waveband. Thus, the concentration measurement and analysis have to be performed after the influence of such unpredictable background is removed. The spectral data from the sample with various backgrounds should be included in a training data set for establishing a robust mathematical model in the near-infrared spectroscopy.

In non-invasive detection of blood glucose concentration, for example, a signal produced by variations of the blood glucose concentration is very weak because the concentration in a body tissue is low and has small variations in a physiological range. On the other hand, extraction of the blood glucose signal is difficult due to light scattering, in addition to light absorption, when the light passes through the body tissue, because the body tissue has complex optical properties. Near-infrared light absorption also exists in water, fat, protein, or the like in the tissue, which may produce signals stronger than that produced by glucose concentration and its variations. Furthermore, a same chemical bond may have multiple absorption peaks from its fundamental frequency absorption or multiplication frequency absorptions distributing on different wavelengths in the given waveband region. And the different molecules in the sample or the body tissue also have various chemical bonds, which may make complicate overlap absorptions in the given near-infrared waveband. Moreover, concentration of substances in the body tissue may also be influenced directly or indirectly by factors such as metabolism, physiological period, and mood fluctuation of a living body, environment, or the like, which makes it difficult to extract the blood glucose concentration information from the recorded optical signals. It is difficult to monitor variations of these factors in real time. Therefore, a reference-based measurement may be employed to solve the above-described problem, because it could be considered as an effective approach to remove some background variations when deducting a background or reference signal from the original data. For example, relative measurement has been applied to realize the blood oxygen saturation measurement for clinical use by referencing to a signal recording at a baseline time.

In ex-vivo experiments, dual optical paths are usually applied to remove common interferences caused by drift of instruments or the like, when setting an analogue for the detection object on the reference optical path. A differential operation is performed by deducting a spectrum from the analogue sample, which has optical properties close to that of the skin or object to be detected, as a background spectrum or a reference spectrum. Experimental results show that such a method can remove influence of the common variation in the measurements effectively.

However, in some applications, such as in the measurement of blood glucose concentration of the human body, it is difficult to find an analogue having optical characteristics close to the human skin tissue and meanwhile containing the skin's variation information during the measurement. Also, in clinical practice of near-infrared non-invasive blood glucose detection, it is difficult to find a body region or skin region with a constant glucose concentration or without any glucose inside as a possible reference position, because glucose exists throughout the whole body and the concentration thereof varies constantly. Thus, the spectral processing method for reducing the background reference applicable in the ex-vivo experiment cannot be used in in-vivo detection directly. Even though a standard reflection plate or a phantom having a reflectivity, which has an order close to that of a diffuse reflectivity of human skin, is introduced into the measurement system as the background reference to remove a part of influence of hardware system reference signals, it is still difficult to obtain the variation signal because light propagation on the reflection plate or the phantom is different from that on the human skin and factors such as metabolism, physiology period, and mood fluctuation of the human body, environment influence or the like cannot be reflected in the spectrum of the standard reflection plate or phantom. This appears to be a great challenge to seek an appropriate reference for performing the reference measurement of blood glucose using the near-infrared spectroscopy.

Thus, in detection of concentration of a particular component in the body tissue using the near-infrared spectroscopy, the measurement may be limited to the approaches for extracting the useful signals, which are disturbed by the varying body background, like the physiological fluctuation of the human body.

Kexin X U, et al., have invented a concentration measurement method using a floating reference position (see, CN patent application published as CN1699973A). A reference which can be used as "background" is found in information contained in the measured spectrum per se, as shown in FIG. 1. Variations of the concentration of the substance to be detected, such as a particular component in the human body, e.g., glucose, may cause variations of optical characteristics, such as absorption coefficient, scattering coefficient, or the like, of the substance to be detected. In a certain radial position $r_k$ from a light source, diffuse light energy is substantially equally varied by absorption and scattering of a tissue and thus remains substantially constant in spite of concentration variation of the glucose. The position $r_k$ is referred to as the floating reference position. The light intensity measured at this position can reflect influence of almost all interference factors other than the glucose concentration variation in the detection process. Thus, the spectrum at this position can be used as the "background" and be subtracted from the spectrum at other positions to extract their glucose specific information. This performing the reference measurement for in-vivo detection appears to be similar to that in the ex-vivo experiments. Existence of the floating reference position has been verified in Monte Carlo simulation and ex-vivo experiments.

However, the reference used as the "background", or the floating reference position, may be different for different subjects to be detected, different skin regions of a subject to be detected, and different light wavelengths, because the light energy variation caused by the blood glucose concentration variation is associated with the optical characteristics of the media, i.e. the body issue.

In the Monte Carlo simulation, palm skin is used as a tissue object for measuring the human body blood glucose concentration. A three-layer skin model including epidermis, dermis, and subcutis is applied in the simulation. A number of incident photons set for the Monte Carlo simulation program is $10^9$. Optical parameters of the three layers given by Maruo, et al. (see, Maruo K., Tsurugi M., Chin J., et al., Noninvasive blood glucose assay using a newly developed near-infrared system, IEEE Journal of Selected Topics in Quantum Electronics, 2003. 9(2): p. 322-330; Maruo K., Oota T., Tsurugi M., et al., New methodology to obtain a calibration model for noninvasive near-infrared blood glucose monitoring, Applied Spectroscopy, 2006. 60(4): p. 441-449) are based on. The optical parameters of the dermis of the skin model vary while the optical parameters of the other layers remain constant when the glucose concentration increases from 0 to 500, 1000, and 1500 mg/dL, respectively. A typical diffuse spectrum distributed across a radial distance of a detector from a light source can be obtained in a wavelength range of 1200-1700 nm when the epidermis, the dermis, and the subcutis of the three-layer skin model is set to 0.5 mm, 3.5 mm, and infinity, as shown in FIG. 2. The distribution is close to exponential distribution, in which diffuse reflection light intensity reduces quickly as the radial distance increases. The diffuse reflection light intensity beyond the radial distance of 2.0 mm is relatively weak, which decreases from $10^{-1}$ to $10^{-8}$.

Radial distributions obtained by subtracting the diffuse reflection light intensity at 0 mg/dL from the diffuse reflection light intensities at different glucose concentrations are shown in FIGS. 3 ($a$1))-($a$3), which correspond to wavelengths of 1200 nm, 1300 nm, 1400 nm respectively, and a float reference positions' distribution on 1200-1400 nm shown in FIG. 3($a$4) thereof. It is clear from the figures that there is a radial position where the diffuse reflection light intensity is insensitive to the glucose concentration variation at respective wavelengths for the given tissue media. Obviously, this position is the floating reference position, and it is dependent on wavelength. The floating reference position changes slightly in a wavelength range of 1200-1300 nm, especially for the shorter wavelength band of 1200-1260 nm. The reference position changes obviously in a wavelength range of 1300-1400 nm. The reference position appears to be closer to the light source as the wavelength becomes longer. The floating reference position does not exist for wavelengths greater than 1400 nm for this media case.

Even at one same wavelength, there may be differences in tissue components for different measurement subjects or media. Also, the tissue components in one same measurement media may change with time. That is, the optical characteristics of a tissue may change. FIG. 3($b$) shows how the floating reference position changes at 1300 nm for the three-layer tissue while the absorption coefficient $\mu_a$ and the scattering coefficient $\mu_s$ change at a gradient of ±20%. The initial optical parameters including $\mu_a$ and $\mu_s$ were applied when the initial body blood glucose concentration was set to 100 mg/dL in the media. As shown in the figure, scattering coefficient varying, which may be induced by different subjects or the different skin tissue regions of a same subject or the same tissue but measured at different conditions etc., could affect the floating reference position obviously.

As a result, the floating reference position may vary at a given wavelength when the tissue layers' thicknesses are varying. FIG. 3($c$) shows how the floating reference position changes in the three-layer skin model at the wavelength of 1300 nm while the thickness of palm epidermis changes in a range of 0.1-1.0 mm and the thickness of the dermis changes in a range of 2.0-4.0 mm. The initial body blood glucose concentration was also set to 100 mg/dL in the simulated media. The floating reference position moves away from the light source as the epidermis thickness increases because the epidermis thickness has a great influence on the diffuse reflection light intensity.

Thus, it is impossible to cover different measurement subjects, a same measurement subject in different states, or a plurality of wavelengths, or even measurement errors may be caused, if a constant radial position is applied as a reference position for the measurement. Therefore, it is desired to develop a more general and robust measurement method suitable for different measurement subjects and wavelengths.

SUMMARY

The present disclosure aims to provide, among others, a more general spectroscopy technique.

According to an aspect of the present disclosure, there is provided a method of processing spectral data, comprising: illuminating a medium to detect an inside particular component with light; obtaining a first spectral data for the medium at a first radial position and a second spectral data for the medium at a second radial position, wherein the first radial position and the second radial position are selected arbitrarily; and performing differential processing on the first spectral data and the second spectral data.

According to a further aspect of the present disclosure, there is provided an optical fiber probe, comprising: a first optical fiber bundle configured to transmit an incident light and having an exit end located at substantially a center of a detection end of the optical fiber probe; a second optical fiber bundle; and a third optical fiber bundle, wherein at the detection end, a distance between an end of an optical fiber included in the second optical fiber bundle and the exit end of the first optical fiber bundle is different from that between an end of an optical fiber included in the third optical fiber bundle and the exit end of the first optical fiber bundle.

According to a still further aspect of the present disclosure, there is provided a method of establishing a prediction model, comprising: performing the above method on a series of media to be detected, wherein each of the series of media contains a background or reference medium with a particular component at a respective known concentration added into the background or reference medium, wherein the reference medium contains the background medium and the particular component at an initial concentration; and establishing the prediction model based on the respective known concentrations and corresponding processed spectral data.

According to a still further aspect of the present disclosure, there is provided a concentration prediction method, comprising: performing the above method on a medium to be detected, which contains a background or reference medium with a particular component at a concentration included in the background or reference medium, which concentration is unknown due to concentration change, wherein the reference medium contains the background medium and the particular component at an initial concentration; and predicting the concentration of the particular component based on the processed spectral data of the medium to be detected and a prediction model.

According to a still further aspect of the present disclosure, there is provided a processing apparatus, comprising: a detector configured to detect spectral data of diffuse light from a medium for determining an inside particular component; and a processor configured to obtain spectral data at a first radial position and a second radial position using the detector and perform differential processing on the detected spectral data, wherein the first radial position and the second radial position are selected arbitrarily.

According to various embodiments of the present disclosure, it is possible to avoid determination of a floating reference position, which may usually be complicated.

BRIEF DESCRIPTION OF THE DRAWINGS

The above and other objects, features, and advantages of the present disclosure will become more apparent from following descriptions on embodiments thereof with reference to attached drawings, in which:

FIG. 3($b$) is a schematic view showing the variation in floating reference position caused by variations in skin optical characteristics;

FIG. 3($c$) is a schematic view showing the variation in floating reference position caused by variations in skin structural characteristics;

DETAILED DESCRIPTION

Hereinafter, descriptions are given with reference to embodiments shown in the attached drawings. However, it is to be understood that these descriptions are illustrative and not intended to limit the present disclosure. Further, in the following, known structures and technologies may be omitted to avoid obscuring the present disclosure unnecessarily.

According to an embodiment of the present disclosure, spectral data at a first radial position and a second radial position, arbitrarily selected and with different distances from a light source, are obtained and then subjected to differential calculation. The inventors have found that such differential calculation can effectively remove various interferences, especially, common-mode interferences. The technology disclosed herein is advantageous over that of CN patent application CN1699973A in that it does not need to determine a reference point.

Figure 4:
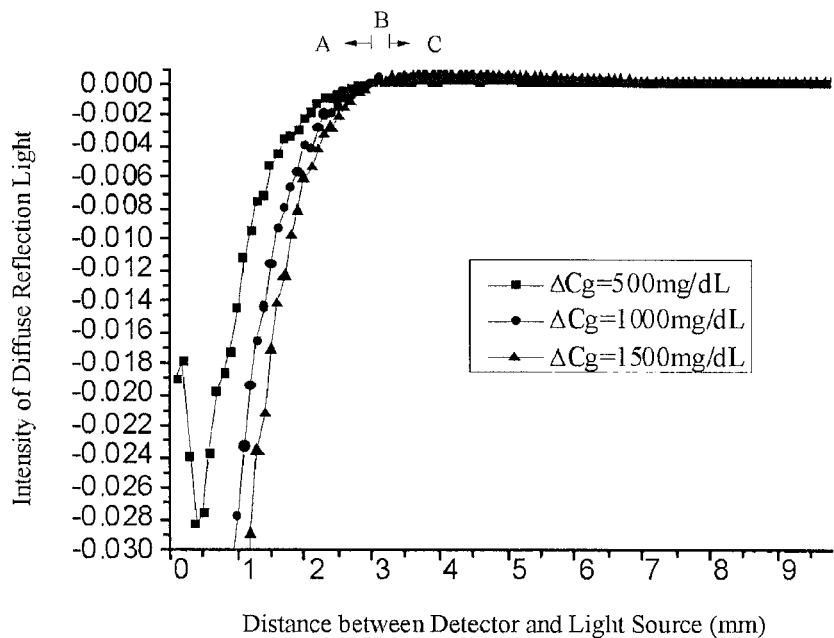
FIG. 4 is a schematic view showing a comparison between spectrum variations in an inner region of a floating reference position and spectrum variations in an outer region of the floating reference position.

The first and second radial positions can be selected as described below in order to achieve better performances, such as interference suppression and effective signal enhancement. For example, the radial positions and optionally a floating reference position can be determined based on a rate of variation in light intensity of diffuse reflection and/or transmission light from a media to be detected at different positions from the light source with respect to a concentration of a particular component, i.e., a component of interest, such as blood glucose, in the medium. Specifically, the floating reference position can be determined as a light reception point having a minimum absolute variation rate (e.g., substantially zero), i.e., a point substantially insensitive to variation in the concentration of the particular component. For example, from Monte Carlo simulation of a typical three-layer model of human skin, a floating reference position for blood glucose concentration measurement is about 1.7-3.2 mm from a light source, which varies in a relatively large range. At a single wavelength of light, taking the floating reference point as a critical point, the intensity of diffuse reflection and/or transmission light decreases in a region inward from the floating reference position and increases in a region outward from the floating reference position as the glucose concentration increases. Consequently, a rate of the variation in intensity of the diffuse reflection and/or transmission light is negative at inner side of the floating reference position and is positive at outer side of the floating reference position, as shown in FIG. 4. Also, the variation in intensity of the diffuse reflection and/or transmission light at a position at the inner side from but close to the floating reference position has an absolute value that has a comparable order with respect to a local maximum of the variation in intensity of the diffuse reflection and/or transmission light. Thus, these two positions can be deemed to have similar sensitivity to variation in glucose concentration. The absolute value of the variation in intensity of the diffuse reflection and/or transmission light increases as the radial distance decreases, i.e., at a position closer to the light source. The absolute value of the variation in intensity of the diffuse reflection and/or transmission light at a position close to the light source is about 100 times of a maximum variation in intensity of the diffuse reflection and/or transmission light at outer side with respect to the floating reference position. Moreover, the diffuse reflection and/or transmission light that exits from epidermis has greater intensity at the position close to the light source.

Figure 5:
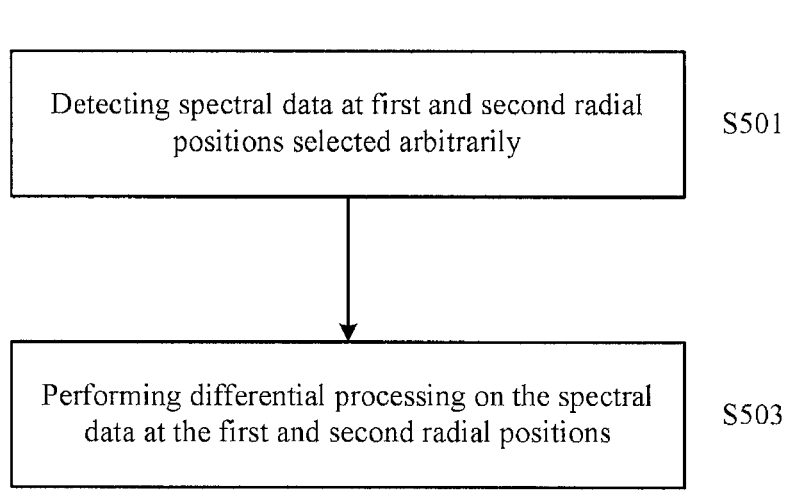
FIG. 5 is a flowchart schematically showing a spectral data processing method according to an embodiment of the present disclosure.

In light of the above characteristics, the present disclosure provides a spectroscopy method. As shown in FIG. 5, the method comprises, at operation S501, measuring a first spectral data for a medium to be detected at a first radial position and a second spectral data for the medium at a second radial position. As described above, the first and second radial positions may be selected arbitrarily. In other words, the first and second radial positions may be selected randomly. The medium to be detected may include any medium, such as human skin or the like. For convenience of description, the medium to be detected may be considered to comprise a background medium and a particular component in the background medium. That is, the background medium may comprise every component in the medium to be detected other than the particular component. The particular component may be any subject of interest, such as blood glucose or the like.

There are various ways in the art to detect the spectrum to obtain the spectral data. For example, the medium to be detected may be illuminated by light at a wavelength from a light source, and diffuse reflection light and/or diffuse transmission light from the medium to be detected can be detected by a detector. For example, the intensity of the light can be detected (the light intensity at a plurality of wavelengths may constitute a spectrum). The following description takes the diffuse reflection light as an example. However, the present disclosure is not limited thereto. Alternatively, the light source and the detector may be immersed into the medium to be detected, to detect the spectral data. This case is similar to the infinite homogeneous medium scenario. The detector can be adjusted in position, to achieve detections at a plurality of radial positions. Alternatively, the detector may comprise two or more light reception units disposed at different positions to detect light intensity at two or more different positions, as described in further detail below.

In addition, light at one or more wavelengths, such as ultraviolet light, visible light and infrared light, may be selected for detection based on characteristics of the medium to be detected and/or the particular component therein. For example, a wavelength at which the scattering and/or absorption characteristics of the particular component are susceptible and/or a wavelength at which the scattering and/or absorption characteristics of the background medium are insusceptible may be selected.

Advantageously, a (absolute and/or relative) variation in light intensity (caused by, for example, a variation in concentration of the particular component in the medium to be detected) may be detected as the spectral data. For example, for the background medium without the particular component or for the background medium with the particular component at a certain initial concentration (the background medium plus the particular component at the initial concentration is called as a reference medium hereinafter), a spectrum may be detected at a radial position as an initial spectrum, marked as $I_1$. Then, when the concentration of the particular component in the background medium is changed with respect to the initial concentration, a spectrum may be detected at this radial position, marked as $I_2$. For example, in a case of blood sugar detection, a spectrum of the blood may be detected in an empty stomach status (in which status the blood sugar is steadily in a relatively low level) as an initial spectrum. Then, a spectrum of the blood may be detected after meal (in which status the blood sugar begins to change until it gradually turns to a steady level by about 2 hours after the meal), to obtain information on the variation of the blood sugar. The (absolute) variation in intensity $s=(I_2-I_1)$ is calculated from the two spectra as the above described spectral data. However, it should be noted that the spectral data is not limited to the absolute variation in intensity, and may comprise other types of data, such as a relative variation in intensity $s=\ln I_2 - \ln I_1$ or $s=(I_2-I_1)/I_1$, as described below.

In various embodiments of the present disclosure, there might be a need for the initial spectrum. In addition to the spectrum detected from the background medium without the particular component, the spectrum detected from the background medium with the particular component at any fixed initial concentration (that is, the reference medium) can be used as the initial spectrum. For example, a database of initial spectra may be established for some media (especially, background media without the particular component), for repeated usage (in pre-experiments or actual detections, for example), so as to reduce workload.

The first and second radial positions may be selected in such a way that the intensity of the diffuse reflection light and/or the diffuse transmission light varies with different variation rates at the two positions with respect to variation in the concentration of the particular component. Also, as there is usually a specific relation between the common-mode interferences at the two positions, the common-mode interferences may be removed by data processing while keeping information related to the concentration variation of the particular component.

Specifically, the first and second radial positions may be selected in such a way that the variation rates of the intensity of the diffuse light may have different signs with respect to the concentration variation of the particular component. Here the "different signs" may include positive (+) and negative (−), positive (+) and zero (0), or negative (−) and zero (0). In other words, in this disclosure, the zero (0) value is considered to have a sign different from positive (+) or negative (−) values. A radial position where the variation rate is zero may be the above-described floating reference position. In actual measurements, a variation rate with an absolute value less than a certain threshold may be considered as the "zero" variation rate. The threshold may be determined according to actual application environments.

As described below, the first and second radial positions selected in this way help to remove the common-mode interference. For example, the first and second radial positions may be selected so that they have a positive variation rate and a negative variation rate, respectively. For example, the variation rate at the first radial position may be negative and the variation rate at the second radial position may be positive. In this case, the first radial position may be in the region (e.g., region A in FIG. 4) inward from the floating reference position (e.g., region B in FIG. 4) while the second radial position may be in the region (e.g., region C in FIG. 4) outward from the floating reference position. Thus, in actual applications, the first radial position may be selected to be close to the light source and the second radial position may be selected to be far away from the light source. Thus, for most cases, the first radial position may be at inner side with respect to the floating reference position and the second radial position may be at outer side with respect to the floating reference position. In this way, the spectral data may be measured at fixed first and second radial positions without having to determine an exact position of the floating reference position. Also, it is possible to provide a detector configuration suitable for various measurement environments, as described below.

Selection of the radial positions may be performed simultaneously with the spectrum detection. For example, first, several radial positions may be selected and the initial spectrum (e.g., light intensity) may be detected at these radial positions or retrieved from the initial spectral database. Next, after the concentration of the particular component in the medium to be detected changes or becomes different from the concentration at which the initial spectral database is established, a changed spectrum (e.g., light intensity) is detected at these radial positions. Signs (positive or negative) of the intensity variation (rates) at the respective radial positions may be determined from the initial spectrum and the changed spectrum. Light intensity (rates) at other radial positions may be obtained by interpolation. A radial position with a position variation and a radial position with a negative variation may be selected as the first and second radial positions, respectively. Alternately, a radial position with a positive or negative variation and a radial position with a variation smaller than a certain threshold (or with a "zero" variation), which may be considered as the floating reference position, may be selected as the first and second radial positions, respectively. The spectral data at the first and second radial positions has already been obtained as described above.

In this way, it is unnecessary to determine the floating reference position in advance, which is complicated because multiple measurements need to be performed to determine a position where the light intensity has a minimum variation. If it happens that the initially-selected radial positions include the floating reference position, the floating reference position can be used, of course. However, this is different from determining the floating reference position in advance and using the spectral data at this position because the inconvenience of determining the floating reference position can be avoided.

According to another embodiment, the floating reference position can be determined. For example, a radial position with the minimum (e.g., substantially zero) absolute variation in light intensity may be selected as the floating reference position. Multiple measurements may be performed around radial positions where the light intensity variation is close to zero to improve position accuracy of the floating reference position. In addition, the spectral data at the floating reference position can also be obtained.

The method further comprises, after obtaining the spectral data at the first and second radial positions, performing differential processing on the spectral data at operation S503.

For example, the differential processing may be performed as follows.

The first radial position is denoted as $\rho_m$ and the second radial position is denoted as $\rho_n$. In particular, a radial position at outer side with respect to the floating reference position may be denoted as $\rho_I$ (with a negative variation rate) and a radial position at outer side with respect to the floating reference position may be denoted as $\rho_O$ (with a positive variation rate). Also, if the floating reference position is predetermined or the selected radial positions include the floating reference position, the floating reference position may be denoted as $\rho_R$.

According to an embodiment of the present disclosure, a weight factor $\eta$ may be determined as follows. A ratio $\eta$ between variations of the diffuse reflection light at two arbitrary radial positions under influence of a factor $\Delta N$, i.e., $\Delta I(\rho_m, C, \Delta N)/\Delta I(\rho_n, C, \Delta N)$ may be determined by numerical computing or by repeatedly detecting the diffuse reflection light at different radial positions while keeping the concentration C of the particular component constant. That is:

$$\Delta I(\rho_m, C, \Delta N) = \eta \cdot \Delta I(\rho_n, C, \Delta N) \qquad (1).$$

Here, $\rho_m$ and $\rho_n$ represent arbitrary radial positions, e.g., any two of $\rho_I$, $\rho_O$, and $\rho_R$. Term $\Delta I(\rho_m, C, \Delta N)$ represents the variation in light intensity at $\rho_m$ caused by the interference factor $\Delta N$ while the concentration C of the particular component is kept constant. Term $\Delta I(\rho_n, C, \Delta N)$ represents the variation in light intensity at $\rho_n$ caused by the interference factor $\Delta N$ while the concentration C of the particular component is kept constant.

In actual detections, the diffuse reflection light may change due to variations in the interference factor, in addition to the concentration variation of the particular component to be detected. When the concentration of the particular component changes by $\Delta C$ and the interference factor changes by $\Delta N$, there exists:

$$\Delta I(\rho_i, \Delta C, \Delta N) = \Delta I(\rho_i, C, \Delta N) + \Delta I(\rho_i, \Delta C, N) \quad (2).$$

Here, $\rho_i$ represents an arbitrary radial position, e.g., any of $\rho_I$, $\rho_O$, and $\rho_R$. Term $\Delta I(\rho_i, \Delta C, \Delta N)$ represents the variation in light intensity at $\rho_i$ caused by the concentration variation $\Delta C$ and the interference factor $\Delta N$. Term $\Delta I(\rho_i, C, \Delta N)$ represents the variation in light intensity at $\rho_i$ caused by the interference factor $\Delta N$. Term $\Delta I(\rho_i, \Delta C, N)$ represents the variation in light intensity at $\rho_i$ caused by the concentration variation $\Delta C$.

Based on equation (1), the spectral data at two arbitrary radial positions, e.g., any two of $\rho_I$, $\rho_O$, and $\rho_R$, may be subjected to the following differential processing:

$$\Delta I_{m-n}(\rho, \Delta C, \Delta N) = \Delta I(\rho_m, \Delta C, \Delta N) - \eta \cdot \Delta I(\rho_n, \Delta C, \Delta N) = \quad (3)$$
$$\Delta I(\rho_m, \Delta C, N) - \eta \cdot \Delta I(\rho_n, \Delta C, N) = \Delta I(\Delta C).$$

From equation (3), it can be seen that noise signals caused by the common-mode interference can be reduced or removed effectively by the differential processing to obtain useful signal $\Delta I(\Delta C)$ only related to the concentration ($\Delta C$) of the particular component to be detected.

It is to be noted that the differential processing is applicable to two arbitrary radial positions $\rho_m$ and $\rho_n$ as can be seen from equation (3), although the following description is about any two of $\rho_I$, $\rho_O$, and $\rho_R$.

Also, the ratio factor $\eta$ between the noise signals caused by the common-mode interference at the two arbitrary radial positions $\rho_m$ and $\rho_n$ can be estimated in advance. In actual detections, this factor may be used directly in the differential processing of the absolute variations in light intensity at the two positions to obtain the useful signal ($\Delta I(\Delta C)$) only related to the concentration ($\Delta C$) of the particular component to be detected.

Next, an expression of $\eta$ is derived from steady-state solution of a diffusion equation in an infinite homogeneous medium, and also an exemplary estimation method of the factor $\eta$ is provided based thereon.

A solution of photon fluence rate $\Phi$ in the infinite homogeneous medium with respect to a point light source is:

$$\Phi(\rho, \lambda, \mu_a, \mu'_s) = \frac{1}{4\pi D} \frac{1}{\rho} \exp(-\mu_{eff}\rho). \quad (4)$$

Here, $\rho$ denotes a radial distance between a detector and the light source; $\lambda$ denotes a wavelength of light emitted from the light source; $\mu_a$ denotes an absorption coefficient; $\mu_s'$ denotes a reduced scattering coefficient and is defined as $(1-g)\mu_s$, where g denotes an anisotropy factor, and $\mu_s$ denotes a scattering coefficient; D denotes a diffusion coefficient of photon and is defined as $D=\{3[\mu_a+(1-g)\mu_s]\}^{-1}=[3(\mu_a+\mu_s')]^{-1}$; $\mu_{eff}$ denotes an effective attenuation coefficient and is defined as $\mu_{eff}=\sqrt{3\mu_a \cdot [\mu_a+(1-g)\mu_s]}=\sqrt{3\mu_a \cdot (\mu_a+\mu_s')}$. Therefore, equation (4) can be transformed to:

$$\Phi(\rho, \lambda, \mu_a, \mu'_s) = \frac{3(\mu_a + \mu'_s)}{4\pi\rho} \exp\left[-\rho\sqrt{3\mu_a \cdot (\mu_a + \mu'_s)}\right]. \quad (5)$$

When incident light enters the medium, photons interact with particles in the medium and exit to generate the diffuse reflection light. Factors causing variations in energy of the diffuse reflection light may be generally classified into three types: (1) variations in optical characteristics of the medium to be detected; (2) drift of an incident light source energy; and (3) drift in states of the detector. When the incident light enters the medium, the photons collide with the particles in the medium. Some photons are absorbed by the particles and other photons are scattered. The variation in optical characteristics of the medium to be detected is a combined result of the absorption and the scattering. Factors causing the variation in optical characteristics, such as absorption coefficient and scattering coefficient, of the medium to be detected mainly include the concentration variation of the particular component to be detected, concentration variation of interference component(s), and temperature variation, or the like. Among the above factors causing the energy variation of the diffuse reflection light, only the concentration variation of the particular component to be detected is desired to be measured, while the energy variation of the diffuse reflection light caused by the other factors should be reduced or removed.

Taking glucose concentration variation in human tissue as an example, according to the steady solution of the diffusion equation in the infinite homogeneous medium, when the blood glucose concentration varies by $\Delta C_g$, a variation $\Delta\varphi(\rho, \Delta C_g)$ in photon fluence rate $\varphi(\rho)$ caused by the concentration variation of the blood glucose at a same radial position is:

$$\Delta\Phi(\rho, \Delta C_g) = \frac{d\Phi(\rho)}{dC_g} \cdot \Delta C_g = \left[\frac{\partial\Phi(\rho)}{\partial\mu_a}\frac{\partial\mu_a}{\partial C_g} + \frac{\partial\Phi(\rho)}{\partial\mu'_s}\frac{\partial\mu'_s}{\partial C_g}\right] \cdot \Delta C_g, \quad (6)$$

wherein:

$$\frac{\partial\Phi(\rho)}{\partial\mu_a} = \frac{1}{4\pi\rho}\left[3 - \frac{\rho}{2}(\mu_{eff}^{-1}D^{-2} + 3\mu_{eff})\right]\exp(-\mu_{eff}\rho); \text{ and} \quad (7)$$

$$\frac{\partial\Phi(\rho)}{\partial\mu'_s} = \frac{1}{4\pi\rho}\left(3 - \frac{3\rho}{2}\mu_{eff}\right)\exp(-\mu_{eff}\rho). \quad (8)$$

As can be seen from equation (6), the variation $\Delta\varphi(\rho, \Delta C_g)$ in the photon fluence rate is a function of the radial distance $\rho$.

According to the definition of the floating reference position, the light reception point where the variation rate of the light intensity is minimum with respect to the concentration variation of the particular component to be detected, i.e., a radial position insensitive to the concentration variation of the particular component, e.g., the blood sugar, is the floating reference position. Thus, in an ideal condition where the blood sugar concentration variation is $\Delta C_g$ and there is no interference factor, at a certain wavelength, sensitivity $\text{Sen}_g(\rho_R)$ at the floating reference position $\rho_R$ for the blood glucose concentration variation according to the steady solution of the diffusion equation in the infinite homogeneous medium is:

$$Sen_g(\rho_R) = \frac{d\Phi(\rho_R)}{dC_g} = \frac{\partial \Phi(\rho_R)}{\partial \mu_a}\frac{\partial \mu_a}{\partial C_g} + \frac{\partial \Phi(\rho_R)}{\partial \mu_s'}\frac{\partial \mu_s'}{\partial C_g} = 0. \quad (9)$$

Substituting equations (7) and (8) into (9), the floating reference position is:

$$\rho_R = \frac{6\left(\frac{\partial \mu_a}{\partial C_g} + \frac{\partial \mu_s'}{\partial C_g}\right)}{(\mu_{eff}^{-1}D^{-2} + 3\mu_{eff})\frac{\partial \mu_a}{\partial C_g} + 3\mu_{eff}\frac{\partial \mu_s'}{\partial C_g}}. \quad (10)$$

At this position, the variation $\Delta\varphi(\rho, \Delta C_g)$ of the photon fluence rate $\varphi(\rho_R)$ caused by the concentration variation of the blood glucose is zero. In actual measurements, the variation of the diffuse reflection light at the floating reference position $\rho_R$ is caused by variation in background interference and is not related to the blood glucose concentration variation, that is:

$$\Delta\Phi(\rho_R,\Delta C_g,\Delta N) = \Delta\Phi(\rho_R,\Delta C_g) + \Delta\Phi(\rho_R,C_g,\Delta N) = \Delta\Phi(\rho_R,C_g,\Delta N) \quad (11).$$

Generally, $\partial\mu_a/\partial C_g$ is smaller than $\partial\mu_s'/\partial C$ by one or more orders, and substituting equation (8) into equation (6) approximately produces:

$$d\Phi \approx \frac{1}{4\pi\rho}\left(3 - \frac{3\rho}{2}\mu_{eff}\right)\exp(-\mu_{eff}\rho) \cdot d\mu_s'. \quad (12)$$

Thus, the variation rate of the diffuse reflection light is:

$$\frac{d\Phi}{\Phi} \approx D\left(3 - \frac{3\rho}{2}\mu_{eff}\right) \cdot \frac{\partial \mu_s'}{\partial C_g} \cdot dC_g. \quad (13)$$

In the equation, $\partial\mu_s'/\partial C_g$ is a variation rate of the reduced scattering coefficient with respect of the glucose concentration variation. Generally, for a fixed mother liquor model, influence of the glucose concentration variation on the reduced scattering coefficient is a constant. For an Intralipid solution model with different concentrations, $\partial\mu_s'/\partial C_g$ may be represented as:

$$\frac{\partial \mu_s'}{\partial C_g} = \mu_s' \cdot m \cdot 2. \quad (14)$$

For a skin (water+polystyrene) model, $\partial\mu_s'/\partial C_g$ may be represented as:

$$\frac{\partial \mu_s'}{\partial C_g} = \mu_s' \cdot m. \quad (15)$$

Figure 6:
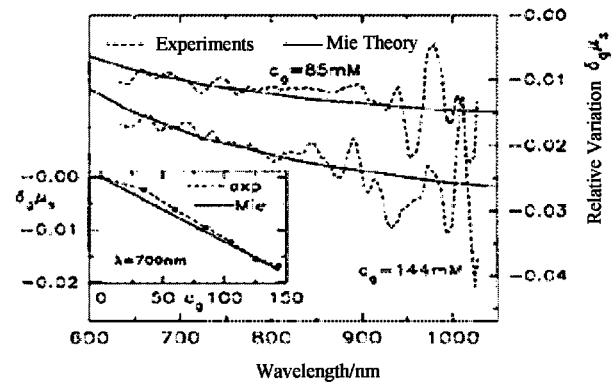
FIG. 6 is a schematic view showing a variation rate of a scattering coefficient in a skin model with respect to wavelength.

In the equation, m is a variation rate of the scattering coefficient with respect to wavelength variation calculated according to the Mie theory, as shown in FIG. 6 (see, Matthias Kohl, Matthias Essenpreis and Mark Cope, The influence of glucose concentration upon the transport of light in tissue-simulating phantoms). The two solid lines in the figure represent variations of the scattering coefficient $\mu_s$ when the glucose concentration is 85 mM/L and 144 mM/L, respectively, in the skin (water+polystyrene) model. The two solid lines can be fitted into straight lines with slopes of $-1.569*10^{-7}$ and $-1.5*10^{-7}$, respectively. Later simulations will be performed using three different gradients of 50, 100, and 150 mM, and thus approximate slopes are used, respectively.

Figure 23:
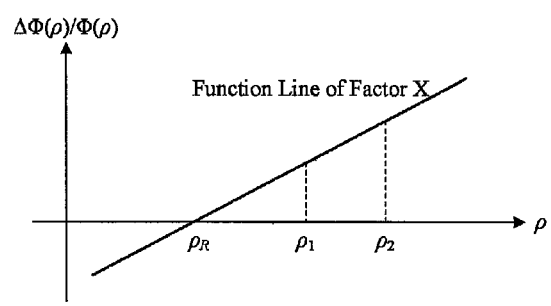
FIG. 23 is a schematic view showing how relative variation in diffuse light varies with respect to radial positions under a factor X.

Thus, the variation rate $d\varphi/\varphi$ of the diffuse reflection light caused by the glucose concentration variation can be considered approximately to be a (substantially linear) function of the radial distance $\rho$, as shown in Equation 13 and FIG. 23.

In actual measurements, there is a fixed ratio between light intensity I and light energy flux density $\varphi$. A relative variation of the light energy flux density approximately equates the relative variation of the light intensity, i.e., $\Delta\Phi/\Phi = \Delta I/I$. Thus, variation of $\Delta I/I$ with respect to detection position is approximately linear.

Thus, the ratio factor $\eta$ between different positions may be derived as follows.

For a same influence factor $\Delta X$, a relative variation in light intensity $\Delta I(\rho_m,\Delta X)/I(\rho_m)$ at a first radial position is used to derive a relative variation in light intensity $\Delta I(\rho_n, \Delta X)/I(\rho_n)$ at a second radial position, by utilizing the fact that $\Delta I(\rho)/I(\rho)$ is a linear function of $\rho$. A ratio between the respective relative variations in light intensity at the first and second radial positions is denoted as $\xi$, which is related to the selection of the radial positions, as can be seen from equation (S-1):

$$\frac{\frac{\Delta I(\rho_m)}{I(\rho_m)}}{\frac{\Delta I(\rho_n)}{I(\rho_n)}} = \frac{\rho_m - \rho_R}{\rho_n\ \rho_R} = \xi. \quad (S-1)$$

In equation (S-1), $\rho_R$ represents a position insensitive to the factor. For example, when the glucose concentration varies, this position may be the floating reference position for glucose measurement. For a particular component to be detected and a particular medium to be detected, it has been proved that the position $\rho_R$ is a relatively stable position. Thus, $\xi$ is a constant if the two measurement positions $\rho_m$ and $\rho_n$ are given in advance. Therefore, the value of $\xi$ can be estimated by experiments in advance.

Equation (S-2) can be derived by transforming equation (S-1):

$$\Delta I(\rho_m) = \xi \cdot \frac{I(\rho_m)}{I(\rho_n)} \cdot \Delta I(\rho_n) = \eta \cdot \Delta I(\rho_n). \quad (S-2)$$

And hence:

$$\eta = \xi \cdot \frac{I(\rho_m)}{I(\rho_n)}. \quad (S-3)$$

As can be seen from equations (S-2) and (S-3), the value of the ratio factor $\eta$ can be obtained by substituting the pre-estimated value of $\xi$ into equation (S-3). The value of $\eta$ may then be substituted into equation (3) to obtain the useful signal ($\Delta/(\Delta C)$), which is only related to the concentration variation ($\Delta C$) of the particular component to be detected.

The interference factor $\Delta N$ in actual measurements, which causes the intensity variation of the diffuse reflection light, may be classified into two types: variations in optical characteristics caused by variation(s) in concentration of interference component(s) in the medium to be detected or variation in measurement temperature; and light source emission drift or detector state drift in the measurement system.

(1) Variations in optical characteristics caused by variation(s) in concentration of interference component(s) in the medium to be detected or variation in measurement temperature The optical characteristics of the medium to be detected will change when the interference component concentration or measurement temperature changes. For example, when the temperature changes, the vibration-rotation state of molecules and probability of transition between energy levels will change. As a result, the Molar extinction coefficient of substance will be different at different temperatures. Meanwhile, temperature variation will cause concentration variation of absorptive substance because temperature increase will enhance bonding degree of chemical bond between the molecules. Thus, a molecule may have an increased number of neighboring molecules, resulting in increased density of the substance. However, the temperature increase may also enlarge distances between the molecules, resulting in decreased density of the substance. A combination of the increase effect and the decrease effect determines how the density of the substance varies with the temperature. If the blood glucose concentration is kept relatively constant at $C_g$ and the temperature changes by $\Delta T$, the variation $\Delta \varphi(\rho, C_g, \Delta T)$ of the photon fluence rate $\varphi(\rho)$ at a same radial position is:

$$\Delta \Phi(\rho, C_g, \Delta T) = \frac{d\Phi(\rho)}{dT} \cdot \Delta T = \left[\frac{\partial \Phi(\rho)}{\partial \mu_a}\frac{\partial \mu_a}{\partial T} + \frac{\partial \Phi(\rho)}{\partial \mu_s'}\frac{\partial \mu_s'}{\partial T}\right] \cdot \Delta T. \quad (16)$$

Substituting equations (7) and (8) into equation (16) produces:

$$\Delta \Phi(\rho, C_g, \Delta T) = \left[\frac{1}{4\pi\rho}\left(3 - \frac{\rho}{2}W\right)\exp(-\mu_{eff}\rho)\frac{\partial \mu_a}{\partial T} + \frac{1}{4\pi\rho}\left(3 - \frac{3\rho}{2}\mu_{eff}\right)\exp(-\mu_{eff}\rho)\frac{\partial \mu_s'}{\partial T}\right] \cdot \Delta T. \quad (17)$$

wherein $W = \mu_{eff}^{-1} D^{-2} + 3\mu_{eff}$.

Next, two positions, which have radial distances $\rho_I$ and $\rho_O$ from the light source, respectively, are used as an inner-side measurement position and an outer-side measurement position with respect to the floating reference position, respectively. According to equation (17), a ratio between the photon fluence rate variation caused by the temperature variation at the inner-side measurement position $\rho_I$ and that at the floating reference position $\rho_R$ and a ratio between the photon fluence rate variation caused by the temperature variation at the outer-side measurement position $\rho_O$ and that at the floating reference position $\rho_R$ are:

$$\frac{\Delta \Phi(\rho_I, C_g, \Delta T)}{\Delta \Phi(\rho_R, C_g, \Delta T)} = \frac{\frac{1}{\rho_I}\left(3 - \frac{\rho_I}{2}W\right)\exp(-\mu_{eff}\rho_I)\frac{\partial \mu_a}{\partial T} + \frac{1}{\rho_I}\left(3 - \frac{3\rho_I}{2}\mu_{eff}\right)\exp(-\mu_{eff}\rho_I)\frac{\partial \mu_s'}{\partial T}}{\frac{1}{\rho_R}\left(3 - \frac{\rho_R}{2}W\right)\exp(-\mu_{eff}\rho_R)\frac{\partial \mu_a}{\partial T} + \frac{1}{\rho_R}\left(3 - \frac{3\rho_R}{2}\mu_{eff}\right)\exp(-\mu_{eff}\rho_R)\frac{\partial \mu_s'}{\partial T}}; \quad (18)$$

and $$\frac{\Delta \Phi(\rho_O, C_g, \Delta T)}{\Delta \Phi(\rho_R, C_g, \Delta T)} = \frac{\frac{1}{\rho_O}\left(3 - \frac{\rho_O}{2}W\right)\exp(-\mu_{eff}\rho_O)\frac{\partial \mu_a}{\partial T} + \frac{1}{\rho_O}\left(3 - \frac{3\rho_O}{2}\mu_{eff}\right)\exp(-\mu_{eff}\rho_O)\frac{\partial \mu_s'}{\partial T}}{\frac{1}{\rho_R}\left(3 - \frac{\rho_R}{2}W\right)\exp(-\mu_{eff}\rho_R)\frac{\partial \mu_a}{\partial T} + \frac{1}{\rho_R}\left(3 - \frac{3\rho_R}{2}\mu_{eff}\right)\exp(-\mu_{eff}\rho_R)\frac{\partial \mu_s'}{\partial T}}, \quad (19)$$

respectively.

Figure 7:
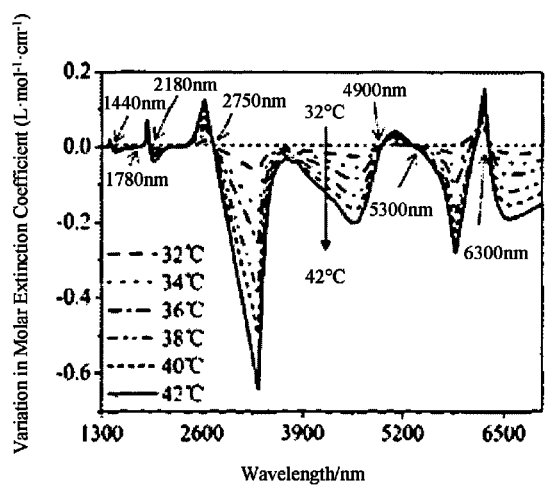
FIG. 7 is a graph showing differences between Molar extinction coefficient $\epsilon_w(\lambda)$ of water at different temperatures and $\epsilon_w(\lambda)$ at 30° C. obtained by experiments of Jensen et al.
Figure 8:
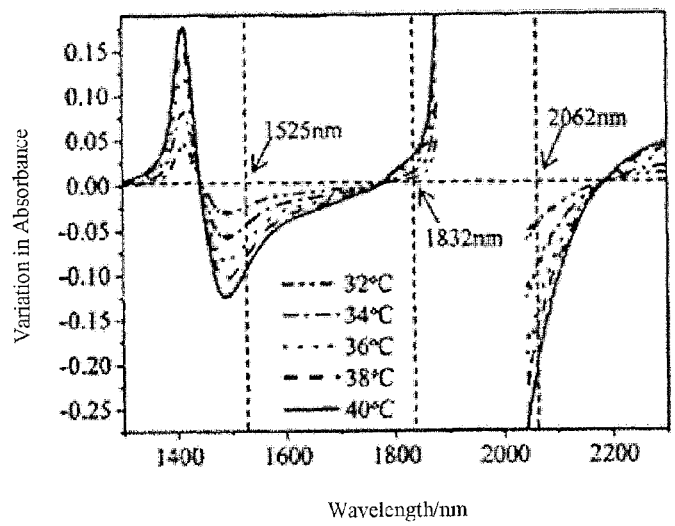
FIG. 8 is a graph showing variation in light absorbance of water between different temperatures and 30° C. obtained by experiments of Yun CHEN et al.

As about 70% of biotic tissue is water, interference of temperature on the biotic tissue in near-infrared spectrum is largely related to temperature characteristics of water spectrum. FIG. 7 shows curves representing differences between Molar extinction of water $\epsilon_w(\lambda)$ at 32° C.-42° C. and that at 30° C., obtained by experiments of Jensen et al. (Peter Snor Jensen, Jimmy Bak, Stenfan Andersson-Engels, Influence of temperature on water and aqueous glucose absorption spectra in the near- and mid-infrared regions at physiologically relevant temperatures, Applied Spectroscopy, 2003, 57(1): 28-36). As shown in the figure, $\epsilon_w(\lambda)$ is insensitive to temperature variation at 1440 nm, 1780 nm, 2180 nm, 2750 nm, 4900 nm, 5300 nm, and 6300 nm, but varies regularly with temperature at other wavelengths. Thus, it can be considered approximately that, within a human body temperature range (about 35° C.-40° C.), a variation rate $\partial \epsilon_w(\lambda)/\partial T$ of the Molar extinction coefficient with respect to the temperature is a constant at respective wavelengths, but having different values for different wavelengths. Thus, it can be considered that a variation rate $\partial \mu_a(\lambda)/\partial T$ of the absorption coefficient with respect to the temperature is also approximately a constant for respective wavelengths. FIG. 8 shows curves representing differences between absorbance of water at various temperatures and that at 30° C., obtained by spectroscopy experiments of Yun CHEN, et al., which are conducted on water samples at 30° C.-40° C. with temperature interval of 2° C. Yun CHEN et al. also obtain a linear function between absorbance variations with respect to temperature at 1525, 2832, and 2060 nm, respectively (Study of Floating Reference Method at Reference Wavelength for Near-infrared Non-invasive Blood Glucose Measurement, Yun CHEN, Tianjin Univ., 2009, [Thesis for Doctor Degree]). As shown in the figure, the absorbance variation with respect to the temperature is approximately linear at respective wavelengths. As water is a pure absorptive medium, a similar conclusion can be obtained that the variation rate $\partial \mu_a(\lambda)/\partial T$ of the absorption coefficient with respect to the temperature is approximately a constant for respective wavelengths.

Laufer et al. study effects of temperature on the optical properties of human dermis and subcutis in a range of 25° C.-40° C. using ex-vivo skin samples (Jan Laufer, et al., Effect of temperature on the optical properties of ex vivo human dermis and subdermis, Phys. Med. Biol., 1998, 43:

2479-2489). Experimental results show that a reduced scattering coefficient of the dermis has a variation rate of $(4.7\pm0.5)\times10^{-3}$ °C.$^{-1}$ with respect to the temperature. A reduced scattering coefficient of the subcutis has a variation rate of $(-1.4\pm0.28)\times10^{-3}$ °C.$^{-1}$ with respect to the temperature. Thus, it can be considered that the reduced scattering coefficient has an approximately constant variation rate $\partial\mu_s'/\partial T$ with respect to the temperature in the human body temperature range (about 35° C.-40° C.).

Thus, as can be seen from equations (18) and (19), when the inner-side measurement position $\rho_I$, the floating reference position $\rho_R$, and the outer-side measurement position $\rho_O$ are determined, the ratios between the photon fluence rate variations ($\Delta\varphi(\rho_I, C_g, \Delta T)/\Delta\varphi(\rho_R, C_g, \Delta T)$ and $\Delta\varphi(\rho_O, C_g, \Delta T)/\Delta\varphi(\rho_R, C_g, \Delta T)$) caused by temperature variation at a same wavelength are both constants, which are denoted as $\eta_1$ and $\eta_2$, respectively, i.e., $$\Delta\Phi(\rho_I, C_g, \Delta T) = \eta_1 \cdot \Delta\Phi(\rho_R, C_g, \Delta T) \quad (20); \text{ and}$$

$$\Delta\Phi(\rho_O, C_g, \Delta T) = \eta_2 \cdot \Delta\Phi(\rho_R, C_g, \Delta T) \quad (21).$$

Thus, the variation in intensity of the diffuse reflection light caused by the temperature variation may be considered as common-mode interference. For a medium to be detected having known optical parameters, the constants $\eta_1$ and $\eta_2$ may be calculated according to equations (18) and (19). For a medium to be detected having unknown optical parameters, the optical parameters thereof may be calculated from the measured diffuse reflection spectrum by reverse construction of the optical parameters and the constants $\eta_1$ and $\eta_2$ may then be calculated according to equations (18) and (19). Alternatively, the variation in intensity of the diffuse reflection light may be measured repeatedly when measurement temperature varies while the blood glucose concentration keeps constant, and the constants $\eta_1$ and $\eta_2$ may be calculated according to equations (20) and (21), e.g., by calculating an average for multiple measurements.

In actual measurements, the temperature variation $\Delta T$ is measured while the glucose concentration varies by $\Delta C_g$. The variation $\Delta\varphi(\rho, \Delta C_g, \Delta T)$ of the photon fluence rate $\varphi(\rho)$ caused by the two factors collectively at a same radial position is:

$$\Delta\Phi(\rho, \Delta C_g, \Delta T) = \quad (22)$$
$$\frac{d\Phi(\rho)}{dC_g}\cdot \Delta C_g + \frac{d\Phi(\rho)}{dT}\cdot \Delta T = \Delta\Phi(\rho, \Delta C_g, T) + \Delta\Phi(\rho, C_g, \Delta T),$$

wherein $\Delta\varphi(\rho,\Delta C_g,T)$ is a useful signal of interest that is to be measured; and $\Delta\varphi(\rho,C_g,\Delta T)$ is a common-mode interference signal related to the radial measurement position.

Thus, according to equations (11) and (22), variations $\Delta\varphi(\rho_I,\Delta C_g,\Delta T)$, $\Delta\varphi(\rho_R,\Delta C_g,\Delta T)$, and $\Delta\varphi(\rho_O,\Delta C_g,\Delta T)$ of the photon fluence rate $\varphi(\rho)$ caused by $\Delta C_g$ and $\Delta T$ collectively at the inner-side measurement position $\rho_I$, the floating reference position $\rho_R$, and the outer-side measurement position $\rho_O$ are:

$$\Delta\Phi(\rho_I, \Delta C_g, \Delta T) = \Delta\Phi(\rho_I, \Delta C_g, T) + \Delta\Phi(\rho_I, C_g, \Delta T) \quad (23);$$

$$\Delta\Phi(\rho_R, \Delta C_g, \Delta T) = \Delta\Phi(\rho_R, \Delta C_g, T) + \Delta\Phi(\rho_R, C_g, \Delta T) = \Delta\Phi(\rho_R, C_g, \Delta T) \quad (24); \text{ and}$$

$$\Delta\Phi(\rho_O, \Delta C_g, \Delta T) = \Delta\Phi(\rho_O, \Delta C_g, T) + \Delta\Phi(\rho_O, C_g, \Delta T) \quad (25), \text{ respectively}.$$

Equations (23) and (24) are subjected to weighted differential operation using equation (20), resulting in:

$$\Delta\Phi_{I-R}(\rho, \Delta C_g, \Delta T) = \Delta\Phi(\rho_I, \Delta C_g, \Delta T) - \eta_1\cdot\Delta\Phi(\rho_R, \Delta C_g, \Delta T) = \quad (26)$$
$$\Delta\Phi(\rho_I, \Delta C_g, T) = \Delta\Phi_1(\Delta C_g).$$

As can be seen from equation (26), the common-mode interference to the diffuse reflection light variation caused by the temperature variation can be removed by the differential operation on the diffuse reflection light variations at the inner-side measurement position $\rho_I$ and the floating reference position $\rho_R$, to obtain the useful signal only related to the blood glucose concentration variation.

Similarly, according to equations (21), (24), and (25), the common-mode interference to the diffuse reflection light variation caused by the temperature variation can also be removed by the differential operation on the diffuse reflection light variations at the outer-side measurement position $\rho_O$ and the floating reference position $\rho_R$:

$$\Delta\Phi_{O-R}(\rho, \Delta C_g, \Delta T) = \Delta\Phi(\rho_O, \Delta C_g, \Delta T) - \eta_2\cdot\Delta\Phi(\rho_R, \Delta C_g, \Delta T) = \quad (27)$$
$$\Delta\Phi(\rho_O, \Delta C_g, T) = \Delta\Phi_2(\Delta C_g).$$

Equations (26) and (27) uses the signals at the inner-side measurement position $\rho_I$ and the outer-side measurement position $\rho_O$, respectively, together with the signal at the floating reference position $\rho_R$, to effectively obtain the useful signal only related to the blood glucose concentration variation and remove the common-mode noise interference.

As can be seen from equations (20) and (21), when the inner-side measurement position $\rho_I$ and the outer-side measurement position $\rho_O$ are determined, a ratio $\Delta\varphi(\rho_I, C_g, \Delta T)/\Delta\varphi(\rho_O, C_g, \Delta T)$ between the photon fluence rate variations at those two positions caused by the temperature variation at a same wavelength is also a constant, which is denoted as $\eta_3$, $$\frac{\Delta\Phi(\rho_I, C_g, \Delta T)}{\Delta\Phi(\rho_O, C_g, \Delta T)} = \frac{\eta_1\cdot\Delta\Phi(\rho_R, C_g, \Delta T)}{\eta_2\cdot\Delta\Phi(\rho_R, C_g, \Delta T)} = \frac{\eta_1}{\eta_2} = \eta_3. \quad (28)$$

i.e., $$\Delta\Phi(\rho_I, C_g, \Delta T) = \eta_3\cdot\Delta\Phi(\rho_O, C_g, \Delta T) \quad (29).$$

Thus, according to equations (23), (25), and (29), the measurement signals at the inner-side and outer-side measurement positions are subjected to differential operation, resulting in:

$$\Delta\Phi_{I-O}(\rho, \Delta C_g, \Delta T) = \Delta\Phi(\rho_I, \Delta C_g, \Delta T) - \eta_3\cdot\Delta\Phi(\rho_O, \Delta C_g, \Delta T) = \quad (30)$$
$$\Delta\Phi(\rho_I, \Delta C_g, T) - \eta_3\cdot\Delta\Phi(\rho_O, \Delta C_g, T) = \Delta\Phi_3(\Delta C_g).$$

As can be seen from equation (30), the common-mode interference to the diffuse reflection light variation caused by the temperature variation may also be removed by the differential operation on the diffuse reflection light variations at the inner-side measurement position $\rho_I$ and the outer-side measurement position $\rho_O$, to obtain the useful signal only related to the blood glucose concentration variation. Also, as can be seen from FIG. 4, the diffuse reflection light variations caused by the blood glucose concentration variation at the inner-side measurement position $\rho_I$ and the outer-side measurement position $\rho_O$ have opposite signs. Therefore, the differential operation as shown in equation (30) increases the weak useful signal in its absolute value, thereby increasing specificity of the signal to be detected and therefore accuracy of measurement results.

Common-mode interference caused by the concentration variation(s) of the interference component(s) in the medium to be detected can be reduced in a similar way.

(2) Light Source Emission Drift or Detector State Drift in Measurement System

The light intensity of the diffuse reflection light may vary when the intensity of the incident light from a light source or the state of a detector for detecting the diffuse reflection light drifts. For example, when the light intensity of the light source drifts, if the blood glucose concentration keeps a constant value $C_g$ and only the light intensity of the light source changes by a factor of $\Delta F$, then a variation $\Delta\varphi(\rho, C_g, \Delta F)$ of photon fluence rate $\varphi(\rho)$ caused thereby at a same radial position is:

$$\Delta\Phi(\rho, C_g, \Delta F) = \Delta F \cdot \Phi_0(\rho) \quad (31),$$

wherein $\varphi_0(\rho)$ represents an initial intensity of the diffuse reflection light at this position. Two positions, which have radial distances $\rho_I$ and $\rho_O$ from the light source, respectively, are used as an inner-side measurement position and an outer-side measurement position with respect to the floating reference position, respectively. According to equation (31), a ratio between the photon fluence rate variation caused by the light intensity drift from the light source at the inner-side measurement position $\rho_I$ and that at the floating reference position $\rho_R$ and a ratio between the photon fluence rate variation caused by the intensity drift from the light source at the outer-side measurement position $\rho_O$ and that at the floating reference position $\rho_R$ are:

$$\frac{\Delta\Phi(\rho_I, C_g, \Delta F)}{\Delta\Phi(\rho_R, C_g, \Delta F)} = \frac{\Delta F \cdot \Phi_0(\rho_I)}{\Delta F \cdot \Phi_0(\rho_R)} = \frac{\Phi_0(\rho_I)}{\Phi_0(\rho_R)}; \quad (32)$$

and $$\frac{\Delta\Phi(\rho_O, C_g, \Delta F)}{\Delta\Phi(\rho_R, C_g, \Delta F)} = \frac{\Delta F \cdot \Phi_0(\rho_O)}{\Delta F \cdot \Phi_0(\rho_R)} = \frac{\Phi_0(\rho_O)}{\Phi_0(\rho_R)}, \quad (33)$$

respectively.

Equations (32) and (33) may be applied to two arbitrary measurement positions. If the equations are transformed, it can be seen that a relative variation in light intensity $$\frac{\Delta\Phi(\rho, C_g, \Delta F)}{\Phi_0(\rho)}$$

at any measurement position is a fixed value. That is, in FIG. 23, when only the light source emission drift interference exists, its function line is a line parallel to the x-axis. In this case, $\xi$ in equation (S-3) is approximately 1 and equation (S-3) may be simplified as equation (S-4), i.e., $$\eta = \frac{I(\rho_m)}{I(\rho_n)}.$$

Figure 24:
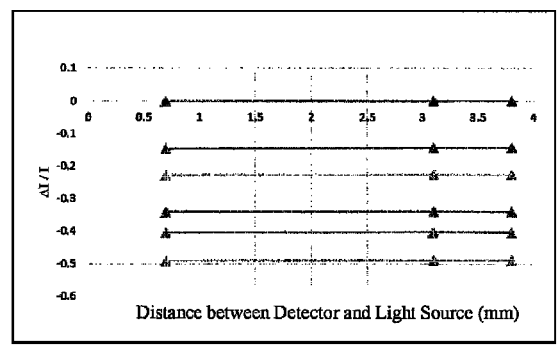
FIG. 24 is a schematic view showing relative variations in light intensity at inner and outer regions of a floating reference position and also at the floating reference position due to variation in light source power.

FIG. 24 shows measurement results of diffuse reflection light for intralipid 3% solution. The light source emission drift is simulated by varying output power of diffuse light. There are three different measurement positions, at which relative variations in light intensity of the diffuse reflection light present a consistent pattern, after five consecutive variations. Thus, the value of $\xi$ may be approximately denoted as 1.

When the inner-side measurement position $\rho_I$, the floating reference position $\rho_R$, and the outer-side measurement position $\rho_O$ are determined, initial intensities of the diffuse reflection light at respective measurement positions are known and fixed, and thus ratios between photon fluence rate variations caused by the intensity drift from the light source at a same wavelength $\Delta\varphi(\rho_I, C_g, \Delta F)/\Delta\varphi(\rho_R, C_g, \Delta F)$ and $\Delta\varphi(\rho_O, C_g, \Delta F)/\Delta\varphi(\rho_R, C_g, \Delta F)$ are both constants, which are denoted as $\eta_4$ and $\eta_5$, respectively, i.e.:

$$\Delta\Phi(\rho_I, C_g, \Delta F) = \eta_4 \cdot \Delta\Phi(\rho_R, C_g, \Delta F) \quad (34); \text{ and}$$

$$\Delta\Phi(\rho_O, C_g, \Delta F) = \eta_5 \cdot \Delta\Phi(\rho_R, C_g, \Delta F) \quad (35).$$

Thus, the intensity variation of the diffuse reflection light caused by the intensity drift from the light source can be considered as a common-mode interference. Values of $\eta_4$ and $\eta_5$ may be calculated according to equations (34) and (35) using variations of the diffuse reflection light repeatedly measured when the blood glucose concentration keeps relatively constant while the temperature changes.

In actual measurements, when the glucose concentration varies by $\Delta C_g$ while the light intensity of the light source drifts by a factor of $\Delta F$, a variation $\Delta\varphi(\rho, \Delta C_g, \Delta F)$ of the photon fluence rate $\varphi(\rho)$ caused by the two factors collectively at a same radial position is:

$$\Delta\Phi(\rho, \Delta C_g, \Delta F) = (1 + \Delta F)\left[\Phi_0(\rho) + \frac{d\Phi(\rho)}{dC_g} \cdot \Delta C_g\right] - \Phi_0(\rho) = \quad (36)$$

$$\Delta F \cdot \Phi_0(\rho) + \frac{d\Phi(\rho)}{dC_g} \cdot \Delta C_g + \Delta F \cdot \frac{d\Phi(\rho)}{dC_g} \cdot \Delta C_g.$$

In actual measurements, $\Delta F$ is in an order of about $10^{-3}$-$10^{-2}$, so the production $$\Delta F \cdot \frac{d\Phi(\rho)}{dC_g} \cdot \Delta C_g$$

may be omitted. Thus, equation (36) may be written as:

$$\Delta\Phi(\rho, \Delta C_g, \Delta F) = \quad (37)$$

$$\Delta F \cdot \Phi_0(\rho) + \frac{d\Phi(\rho)}{dC_g} \cdot \Delta C_g = \Delta\Phi(\rho, C_g, \Delta F) + \Delta\Phi(\rho, \Delta C_g, F),$$

wherein $\Delta\varphi(\rho, C_g, \Delta F)$ is a common-mode interference signal related to the radial measurement position, and $\Delta\varphi(\rho, \Delta C_g, F)$ is a useful signal of interest to be measured.

According to equations (11) and (37), variations $\Delta\varphi(\rho_I, \Delta C_g, \Delta F)$, $\Delta\varphi(\rho_R, \Delta C_g, \Delta F)$, and $\Delta\varphi(\rho_O, \Delta C_g, \Delta F)$ of the photon fluence rate $\varphi(\rho)$ collectively caused by $\Delta C_g$ and $\Delta F$ at the inner-side measurement position $\rho_I$, the floating reference position $\rho_R$, and the outer-side measurement position $\rho_O$ are:

$$\Delta\Phi(\rho_I, \Delta C_g, \Delta F) = \Delta\Phi(\rho_I, \Delta C_g, F) + \Delta\Phi(\rho_I, C_g, \Delta F) \quad (38);$$

$$\Delta\Phi(\rho_R, \Delta C_g, \Delta F) = \Delta\Phi(\rho_R, \Delta C_g, F) + \Delta\Phi(\rho_R, C_g, \Delta F) = \Delta\Phi(\rho_R, C_g, \Delta F) \quad (39); \text{ and}$$

$$\Delta\Phi(\rho_O, \Delta C_g, \Delta F) = \Delta\Phi(\rho_O, \Delta C_g, F) + \Delta\Phi(\rho_O, C_g, \Delta F) \quad (40), \text{ respectively.}$$

Differential operation on equations (38) and (39) using equation (34) produces:

$$\Delta\Phi_{I-R}(\rho, \Delta C_g, \Delta F) = \Delta\Phi(\rho_I, \Delta C_g, \Delta F) - \eta_4 \cdot \Delta\Phi(\rho_R, \Delta C_g, \Delta F) = \quad (41)$$
$$\Delta\Phi(\rho_I, \Delta C_g, F) = \Delta\Phi_4(\Delta C_g).$$

As can be seen from equation (38), the common-mode interference to the diffuse reflection light variation caused by the light intensity drift from the light source can be removed by the differential operation on the diffuse reflection light variations at the inner-side measurement position $\rho_I$ and the floating reference position $\rho_R$, to obtain an useful signal only related to the blood glucose concentration variation.

Similarly, according to equations (35), (39), and (40), the common-mode interference to the diffuse reflection light variation caused by the light intensity drift from the light source can also be removed by the differential operation on the diffuse reflection light variations at the outer-side measurement position $\rho_O$ and the floating reference position $\rho_R$ as follows:

$$\Delta\Phi_{O-R}(\rho, \Delta C_g, \Delta F) = \Delta\Phi(\rho_O, \Delta C_g, \Delta F) - \eta_5 \cdot \Delta\Phi(\rho_R, \Delta C_g, \Delta F) = \quad (42)$$
$$\Delta\Phi(\rho_O, \Delta C_g, F) = \Delta\Phi_5(\Delta C_g).$$

Equations (41) and (42) uses the signals at the inner-side measurement position $\rho_I$ and the outer-side measurement position $\rho_O$, respectively, together with the signal at the floating reference position $\rho_R$, to effectively obtain the useful signal only related to the blood glucose concentration variation and remove the common-mode noise interference.

As can be seen from equations (34) and (35), when the inner-side measurement position $\rho_I$ and the outer-side measurement position $\rho_O$ are determined, a ratio $\Delta\varphi(\rho_I, C_g, \Delta F)/\Delta\varphi(\rho_O, C_g, \Delta F)$ between photon fluence rate variations at those two positions caused by the light intensity drift from the light source at a same wavelength is also a constant, which is denoted as $\eta_6$, i.e., $$\frac{\Delta\Phi(\rho_I, C_g, \Delta F)}{\Delta\Phi(\rho_O, C_g, \Delta F)} = \frac{\eta_4 \cdot \Delta\Phi(\rho_R, C_g, \Delta F)}{\eta_5 \cdot \Delta\Phi(\rho_R, C_g, \Delta F)} = \frac{\eta_4}{\eta_5} = \eta_6, \quad (43)$$

i.e., $$\Delta\Phi(\rho_I, C_g, \Delta F) = \eta_6 \cdot \Delta\Phi(\rho_O, C_g, \Delta F) \quad (44)$$

Thus, according to equations (38), (40), and (44), differential operation on the measurement signals at the inner-side and outer-side measurement positions will result in:

$$\Delta\Phi_{I-O}(\rho, \Delta C_g, \Delta F) = \Delta\Phi(\rho_I, \Delta C_g, \Delta F) - \eta_6 \cdot \Delta\Phi(\rho_O, \Delta C_g, \Delta F) = \quad (45)$$
$$\Delta\Phi(\rho_I, \Delta C_g, F) - \eta_6 \cdot \Delta\Phi(\rho_O, \Delta C_g, F) = \Delta\Phi_6(\Delta C_g).$$

As can be seen from equation (45), the common-mode interference to the diffuse reflection light variation caused by the intensity drift from the light source may also be removed by the differential operation on the diffuse reflection light variations at the inner-side measurement position $\rho_I$ and the outer-side measurement position $\rho_O$, to obtain the useful signal only related to the blood glucose concentration variation. This can increase the universality of the floating reference measurement method and increase an absolute value of the weak useful signal.

Common-mode interference caused by the state drift of the detector for detecting the diffuse reflection light intensity can be reduced in a similar way.

It can be seen that, at operation S503, the spectral data at the first and second radial positions are subjected to differential processing to remove the common-mode interferences caused by two different interference factors using the weighted differential operation as described in equation (3). Diffuse reflection light signals measured at other different wavelengths may be modified in a similar way to obtain effective signals $\Delta\varphi(\lambda_i, C_g)$ at the respective wavelengths processed by the weighted differential processing.

According to embodiments of the present disclosure, spectrum signals at different positions may be detected by different reception manners.

Figures 9A, 9B:
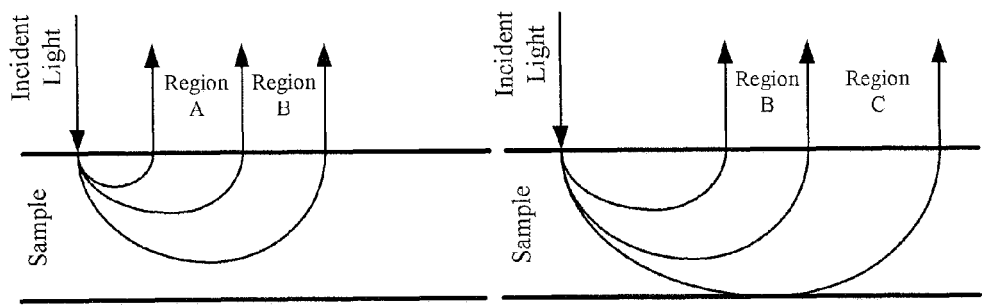
FIGS. 9($a$)-9($d$) are schematic views showing a segmented reception strategy according to an embodiment of the present disclosure.

When the floating reference position does not change much for different measurement parts in one same medium to be detected, different measurement wavelengths, or different media to be detected, the diffuse reflection spectrum at different positions may be obtained as below:

1) A spectrum signal at an inner side (e.g., region A in FIG. 4) from the floating reference position with respect to the light source is received as a measurement point, and a spectrum signal at the floating reference position (e.g., region B in FIG. 4) is received as a reference point, as shown in FIG. 9(a).

2) A light reception point where the absolute variation rate is minimal is selected as the floating reference position (e.g., point B), and a light reception point (e.g., region C in FIG. 4) where the variation rate is locally maximal is selected as a measurement point, as shown in FIG. 9(b).

Figures 9C, 9D:
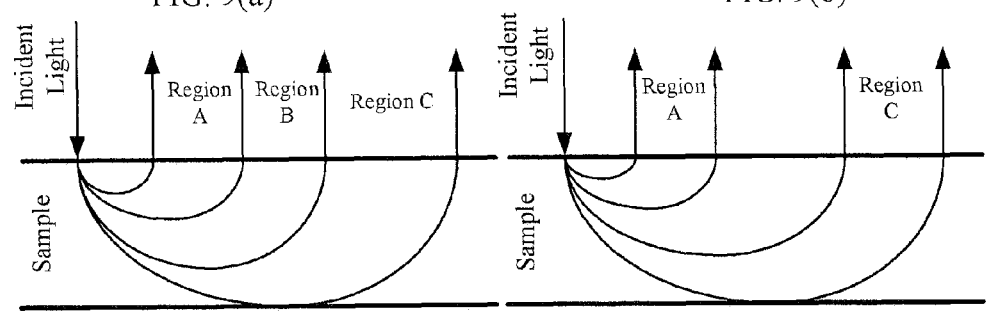

3) Spectrum signals at the inner-side position (e.g., region A in FIG. 4) from the floating reference position with respect to the light source, the floating reference position (e.g., point B), and the outer-side position (e.g., region C in FIG. 4) from the floating reference position with respect to the light source are all received, and the spectrum signals at the inner-side and outer-side positions are subjected to weighted differential processing, as shown in FIG. 9(c).

Figure 1:
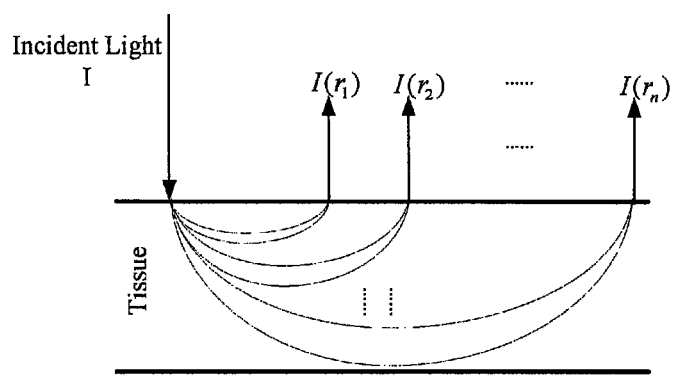
FIG. 1 is a schematic view showing a measurement principle of a floating reference position.
Figure 2:
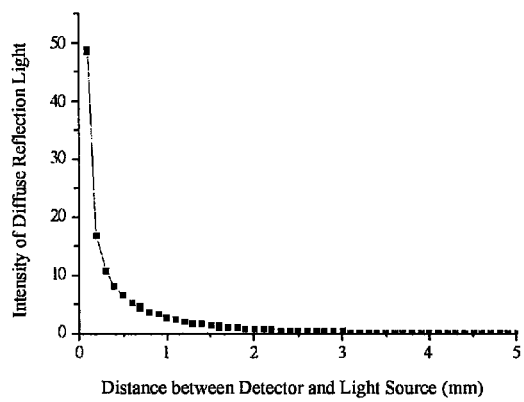
FIG. 2 is a schematic view showing a radial distribution of a typical diffuse reflection spectrum.
Figure 3:
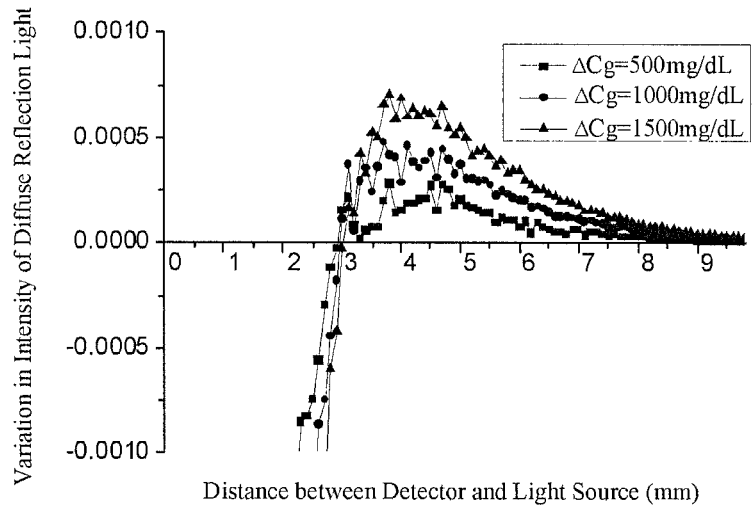
FIGS. 3($a$1)-3($a$4) are schematic views showing the variation in floating reference position caused by different wavelengths.
Figure 3:
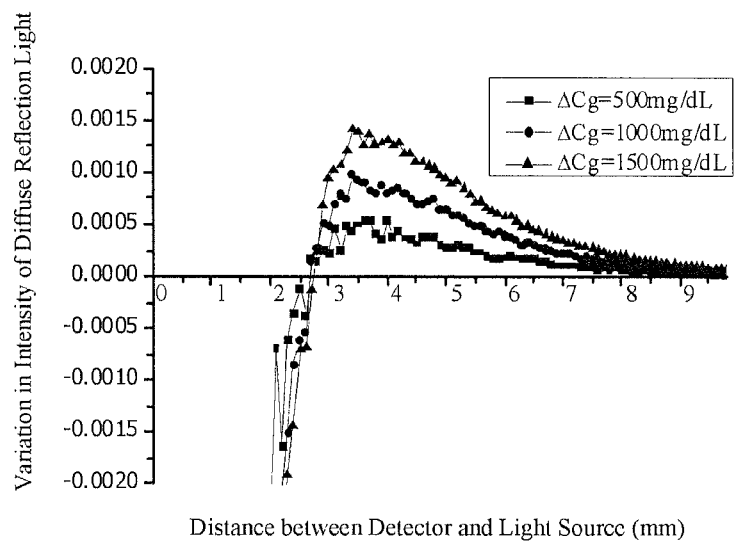
Figure 3:
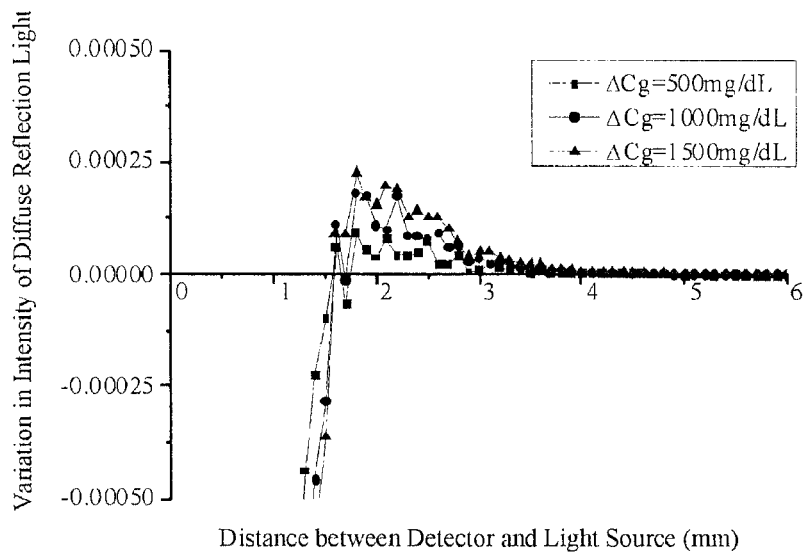
Figure 3:
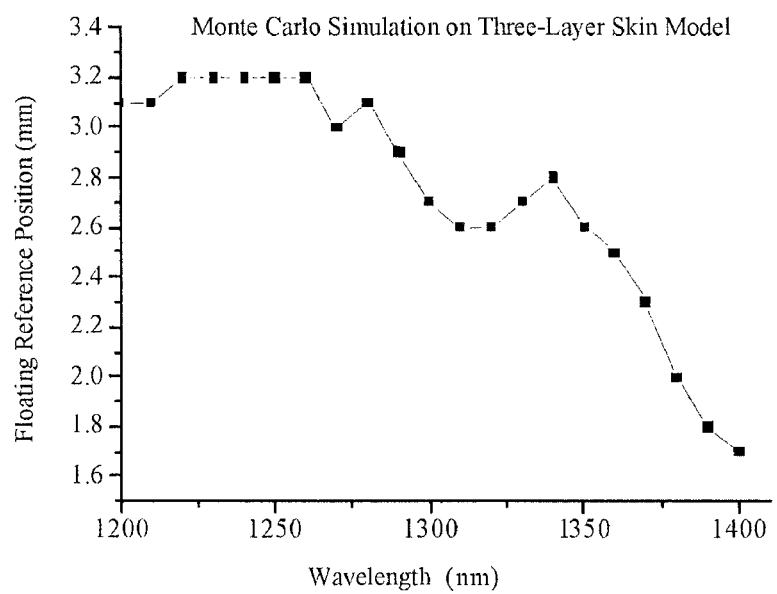
Figure 3B:
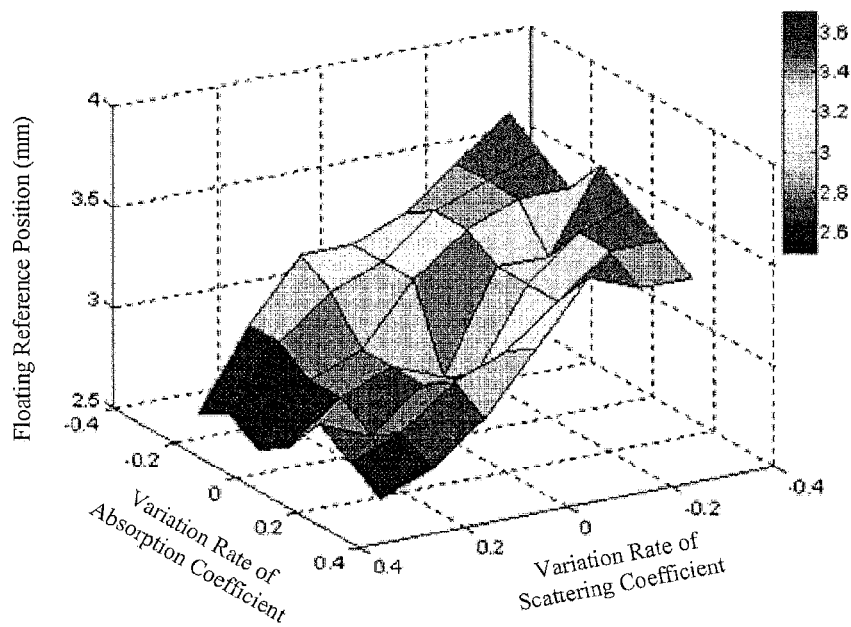
Figure 3C:
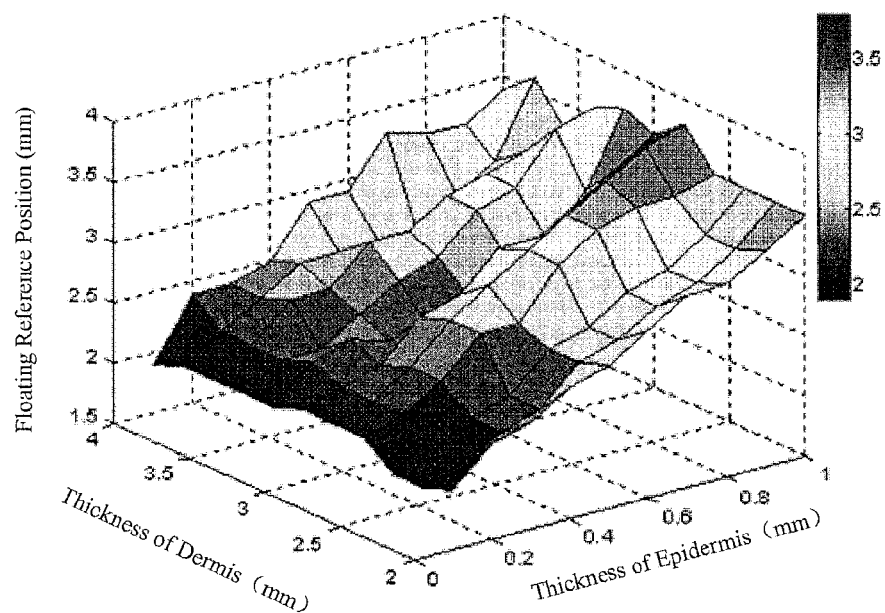

When the floating reference position changes obviously for different measurement parts in the same medium to be detected, different measurement wavelengths, or different media to be detected and thus cannot be easily determined, the diffuse reflection spectrum at different positions may be obtained as below. In particular, for different measurement parts of the same media to be detected, different wavelengths, or different media to be detected, as different optical parameters may have obvious influence on determination of the floating reference position, the floating reference position may change as the measurement position or the measurement wavelength changes, as shown in FIG. 3. Thus, in consideration that the inner side and outer side of the floating reference position with respect to the light source contain similar noise information, reception radius at the inner side of the floating reference position may be reduced properly and reception radius at the outer side of the floating reference position may be increased properly to ensure the floating reference position at respective wavelengths or for different parts is not involved. Diffuse reflection light is received at a position (e.g., region A in FIG. 4) having a radius smaller than that of the floating reference position and a position (e.g., region C in FIG. 4) having a radius smaller than that of the floating reference position, and then the spectral data from the inner and outer sides of the floating reference position are subjected to weighted differential operation, as shown in FIG. 9(d).

Figure 10A:
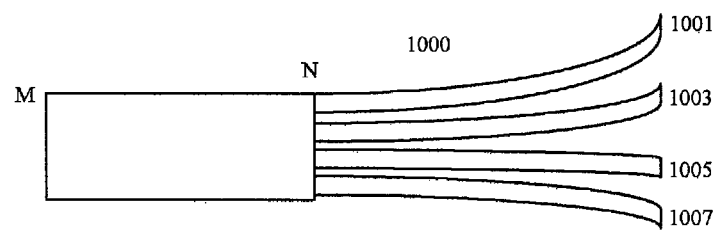
FIGS. 10($a$)-10($e$) are schematic views showing an optical fiber probe according to an embodiment of the present disclosure, wherein FIG. 10 ($a$) is a side view and FIGS. 10($b$)-10($e$) are sectional views.

FIG. 10(a) schematically shows an optical fiber probe according to an embodiment of the present disclosure. As shown in FIG. 10, the optical fiber probe 1000 comprises a plurality of fiber bundles 1001, 1003, 1005, and 1007 wrapped by a cladding layer. Each of the fiber bundles may comprise one or more optical fibers. The fiber bundle 1001 may be configured to direct incident light from a light source. The fiber bundles 1003, 1005, and 1007 may be configured to direct diffuse reflection light from a medium to be detected. More specifically, the fiber bundle 1003 may be configured to direct the diffuse reflection light from a radial position at an inner side with respect to the floating reference position. The fiber bundle 1005 may be configured to direct the diffuse reflection light from the floating reference position. The fiber bundle 1007 may be configured to direct the diffuse reflection light from a radial position at an outer side with respect to the floating reference position. These fiber bundles converge from an end N. The incident light directed in the fiber bundle 1001 may exit from an end M. The fiber bundles 1003, 1005, and 1007 may receive the diffuse reflection light from the end M. Thus, the end M may be referred to as a detection end of the optical fiber probe 1000.

It should be noted that the fibers are divided into "fiber bundles" logically according to their respective functions. These fibers, however, may be mingled with each other without being separated physically.

Although FIG. 10(a) shows four fiber bundles, the present disclosure is not limited thereto. More or less fiber bundles may be included. Furthermore, arrangement of the fiber bundles is not limited as shown in FIG. 10(a). For example, the fibers of respective fiber bundles may interleave with each other in the cladding layer.

FIGS. 10(b) to 10(e) schematically show sectional views of optical fiber probes at the end M according to various embodiments of the present disclosure.

Figure 10B:
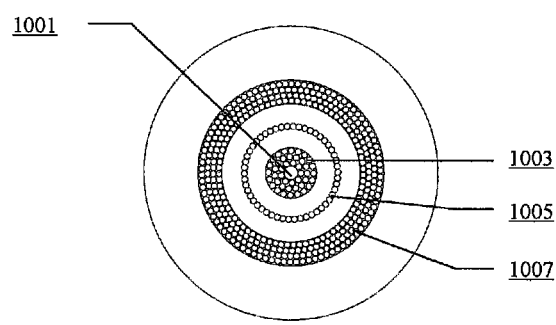

As shown in FIG. 10(b), the fiber bundle 1001 for directing the incident light may be arranged at an approximate center. The fiber bundle 1003 may be arranged around the fiber bundle 1001. The fiber bundle 1007 may be arranged around and relatively far away from the fiber bundle 1001. The fiber bundle 1005 may be arranged between the fiber bundle 1003 and the fiber bundle 1007 around the fiber bundle 1001. The optical fiber probe may be designed to have different dimensions according to different floating reference positions for different media to be detected.

In actual measurements, the optical fiber probe 1000 may be placed in such a way that an end of the fiber bundle 1005 is substantially in alignment with the floating reference position, if the floating reference position exists and its rough range has been determined or known. Diffuse reflection light signals from the fiber bundles 1003, 1005, and 1007, i.e., from the floating reference position, the inner-side position with respect to the floating reference position, and the outer-side position with respect to the floating reference position, may be extracted. Alternatively, only the diffuse reflection light signals from the fiber bundles 1003 and 1007, i.e., from the inner-side position with respect to the floating reference position and the outer-side position with respect to the floating reference position, may be extracted, if the floating reference position is not determined exactly or the end of the fiber bundle 1005 is roughly in alignment with an approximate region of the floating reference position but is not in exact alignment with the floating reference position. Alternatively, the diffuse reflection light signals from the fiber bundles 1003 and 1005, i.e., from the inner-side position with respect to the floating reference position and the floating reference position, or the diffuse reflection light signals from the fiber bundles 1005 and 1007, i.e., from the floating reference position and the outer-side position with respect to the floating reference position, may be extracted.

Figure 10C:
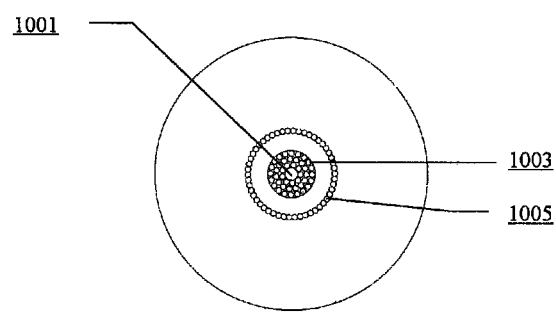

FIG. 10(c) schematically shows a configuration where there are the fiber bundles 1001, 1003, and 1005, but without the fiber bundle 1007. In this configuration, spectrum signals from the inner-side position with respect to the floating reference position and the floating reference position may be received.

Figure 10D:
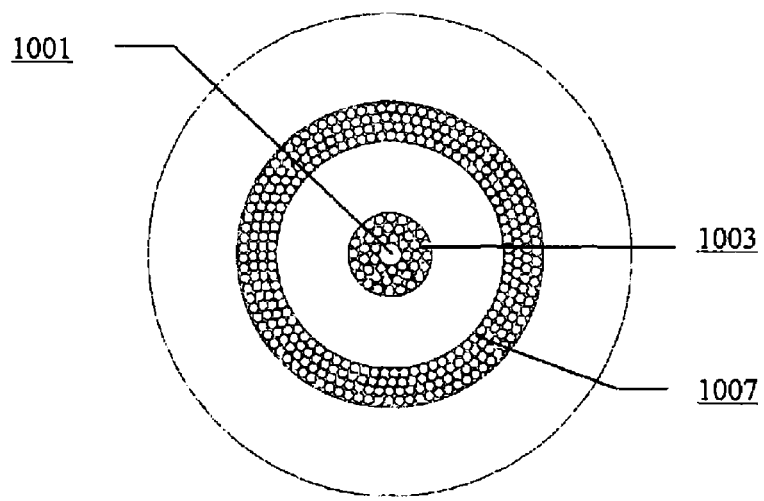

FIG. 10(d) schematically shows a configuration where there are the fiber bundles 1001, 1003, and 1007, but without the fiber bundle 1005. In this configuration, spectrum signals from the inner-side position with respect to the floating reference position and the outer-side position with respect to the floating reference position may be received.

Figure 10E:
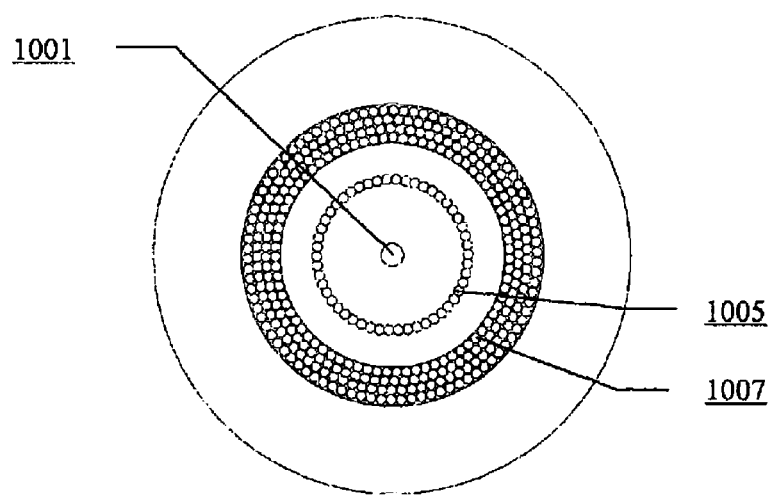

FIG. 10(e) schematically shows a configuration where there are the fiber bundles 1001, 1005, and 1007, but without the fiber bundle 1003. In this configuration, spectrum signals from the floating reference position and the outer-side position with respect to the floating reference position may be received.

Generally, a distances between the end of the fiber bundle 1005 in alignment with the floating reference position and that of the fiber bundle 1001 may be an approximately fixed value. In the above configuration, the end of the fiber bundle 1005 is a circle having a fixed radius around the end of the fiber bundle 1001. A distance between an end of each of the other fiber bundles 1003/1007 and that of the fiber bundle 1001 may cover a certain range. In the above configuration, the ends of the fiber bundles 1003/1007 are rings around the fiber bundle 1001.

Although the ends of the fibers included in each of the fiber bundles 1003, 1005, and 1007 are shown in FIGS. 10(b)-10(e) as arranged closely in a circle or ring around the fiber bundle 1001, the present disclosure is not limited thereto. For example, they may be arranged not closely, but sparsely with respect to each other (and thus spaced apart from each other). Alternatively, the fibers may not constitute a whole circle or ring but may be only a part of such patterns.

In actual measurements, the measurement position and the floating reference position may comprise a physically-realizable point. However, the incident and/or exit light may take a shape constituted by multiple points of similar characteristics, such as circle, ring, or rectangular, etc.

According to an embodiment of the present disclosure, relative variations in light intensity may be used as the spectral data for the differential processing to keep only measurement information related to concentration variation.

The inventors have found that the relative intensity variation is linear or substantially linear along the radial position ρ. As described above, e.g., with reference to FIG. 23, the above differential processing is also applicable to the relative intensity variations. For example, multiplicative noise may be removed by directly performing the differential processing on the relative intensity variations at two radial positions. Additive noise may be removed by performing the weighted differential processing by the factor n on the relative intensity variations at two radial positions, as described above.

Figure 11:
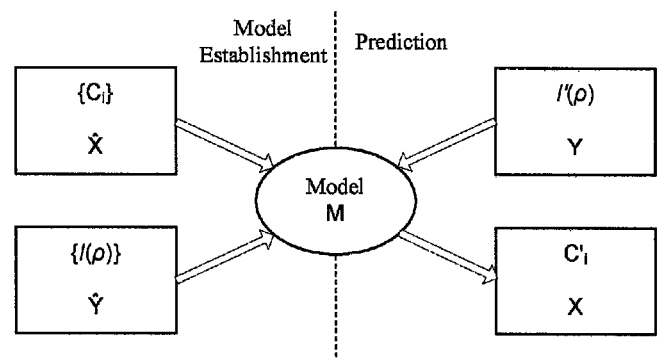
FIG. 11 is a schematic view showing a general principle of concentration prediction model establishment and concentration prediction.

FIG. 11 shows a general principle of concentration prediction based on spectral data. As shown in FIG. 11, a particular component may be added into a background medium or a reference medium (including the background medium and the particular component at an initial concentration) at a series of known concentrations $\{C_i\}$, from which a series of respective diffuse spectral data $\{I(\rho)\}$ may be obtained. Based on a data set $\hat{X}$ of those known concentrations and a set $\hat{Y}$ of the respective diffuse spectral data, a prediction model M can be established. Then, for the background or reference medium with the particular component at an unknown concentration (or with an unknown concentration variation) $C'_t$, corresponding spectral data $I'(\rho)$ ("Y") may be obtained. The concentration ("X") can be predicted based on $I'(\rho)$ according to the prediction model M.

As described above, the spectral data may comprise any suitable forms of data, such as the variation in light intensity or the relative variation in light intensity.

In the model establishment, the spectrum of the background or reference medium may be used as an initial spectrum, and the spectra measured after the particular component is added at the known concentrations $\{C_i\}$ may be used as measured spectra. Thus, the variation in light intensity may be determined therefrom. Likewise, in the prediction, the spectrum of the background or reference medium (the initial concentration of the particular component in the reference medium may be the same as or different from the initial concentration of the particular component in the reference medium used in the model establishment) may be used as an initial spectrum, and the spectrum measured after the concentration of the particular component is changed may be used as the measured spectrum. Thus, the variation in light intensity may be determined therefrom. A result of the prediction may comprise a relative value of the concentration (i.e., a variation amount of the concentration), and may be converted to a predicted concentration by adding it to the initial value (zero in case of the background medium, or the initial concentration in case of the reference medium).

According to embodiments of the present disclosure, those spectral data may be subjected to the above differential processing to effectively remove influence of interference factors. The prediction model M may be established by a chemical metrology method. For example, the data after being subjected to the differential processing may be used for establishing the model using the partial least square (PLS) method and a pure signal model may then be established.

The prediction model M may be established in advance for the background/reference medium and the particular component and stored in, e.g., a database or server. The prediction model M may be retrieved from the database or server when necessary.

Figure 12:
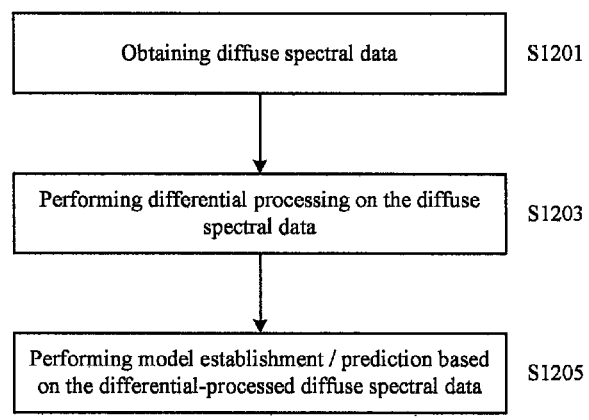
FIG. 12 is a flowchart showing a prediction model establishment/concentration prediction method according to an embodiment of the present disclosure.

According to an embodiment of the present disclosure, there is provided a model establishment and/or concentration prediction method. Referring to FIG. 12, at operation S1201, spectral data may be obtained. For example, in the model establishment, the spectral data may be obtained from the background or reference medium with the particular component added at the known concentrations $\{C_i\}$ (for example, the data may comprise the variation in light intensity after addition of the particular component as compared with before addition of the particular component); while in the prediction, the spectral data may be obtained from the background or reference medium with the particular component whose concentration is changed (for example, the data may comprise the variation in light intensity after the concentration is changed as compared with before the concentration is changed). Next, at operation S1203, the spectral data may be subjected to differential processing, for example, spectral data at two different positions, at which light intensity variations have different signs, is subjected to the differential processing. Then, at operation S1205, the model establishment or the concentration prediction may be performed based on the processed differential signal. The process of FIG. 12 applies in almost the same way in the model establishment and in the concentration prediction, except that: in the model establishment, the concentrations of the particular component are known, and the prediction model (M) is established from the concentrations ($\hat{X}$) and the spectral data ($\hat{Y}$); while in the concentration prediction, the concentration (or concentration change) of the particular component is unknown, and the concentration (or concentration change) (X) is predicted from the spectral data (Y) according to the prediction model (M).

According to an embodiment of the present disclosure, the model establishment/prediction method may be applied in non-invasive blood glucose concentration measurement of human body. In this case, the applied light may have a wavelength in a range of about 1.0-2.4 μm.

In an example, a floating reference position for 5% intralipid solution may be determined by Monte Carlo simulation, and emission drift of light source may be simulated by changing a number of incident photons.

Figure 13:
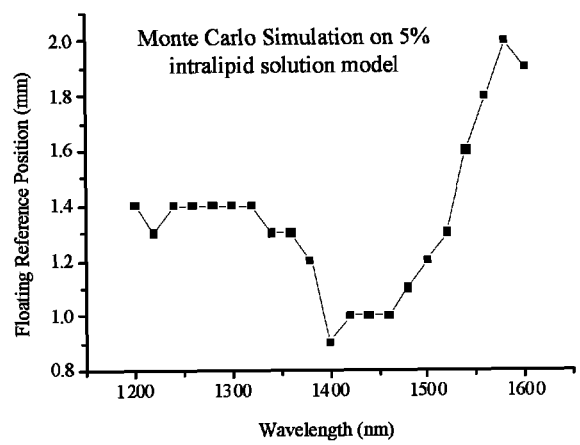
FIG. 13 is a schematic view showing calculation results of floating reference position for 5% intralipid solution by Monte Carlo simulation.
Figure 14:
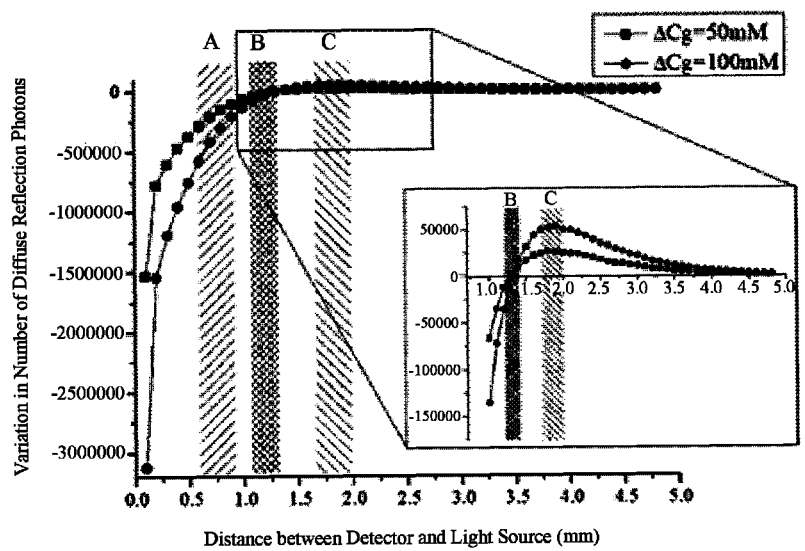
FIG. 14 is a schematic view showing variations in number of diffuse reflection photons when a glucose concentration in 5% intralipid solution changes by 50 mM and 100 mM, respectively.

FIG. 13 schematically shows Monte Carlo simulation results of the floating reference position for the 5% intralipid solution. Optical parameters used in the simulation include absorption coefficient, scattering coefficient, anisotropy factor, and diffusion factor from Tamara L. Troy & Suresh N. Thennadil, Optical properties of human skin in the near infrared wavelength range of 1000 to 2200 nm, Journal of Biomedical Optical, 2001, 6(2):167-176. Wavelength of the simulation is in a range of 1100-1600 nm. Glucose concentration is in a range of 0-100 mM with an interval of 10 mM. A number of photons is $10^9$. Differences in light intensity between respective diffuse reflection light detected from the intralipid solution having the respective glucose concentrations and diffuse reflection light detected from pure intralipid solution containing no glucose show that the floating reference position varies in a range of about 0.9-2 mm in a wavelength range of 1100-1600 nm. This indicates that the floating reference position of a same subject to be detected or sample may vary obviously for different wavelengths Thus, the diffuse reflection light reception scheme as shown in FIG. 9(d) may be used. Specificity, spectra from two positions at inner side and outer side of the floating reference position with respect to a light source is received. FIG. 14 shows variations in number of diffuse reflection photons when the glucose concentration changes by 50 mM and 100 mM, respectively, at a wavelength of 1300 nm in a case where the number of incident photons is $10^9$.

Generally, a measured signal may be separated into a useful signal $I_S$ generated by the glucose concentration variation and a noise signal $I_N$ associated with human physical background or outer environment changes, i.e., $$I(\rho)=I_S(\rho)+I_N(\rho) \quad (46).$$

$I_S$ is associated with the glucose concentration $C_g$, and $I_N$ is caused mainly by physical factors such as light source emission drift, temperature, pressure, and displacement, or the like. Here, only noise interference caused by the light source emission drift is considered. Thus, a variation in measured light intensity caused by the light source emission drift and the blood glucose concentration variation is:

$$\Delta I(\rho,\Delta C_g,\Delta N)=\Delta I_S(\rho,\Delta C_g,N)+\Delta I_N(\rho,C_g,\Delta N) \quad (47)$$

Here, ρ represents a radial distance between a detector and the light source, i.e., a radial position in a spherical coordinate system for the Monte Carlo simulation, $\Delta C_g$ represents the blood glucose concentration variation, $\Delta N$ represents background variation, $\Delta I_S(\rho, \Delta C_g, N)$ represents effective glucose concentration information, which is desired. A background interference signal $\Delta I_N(\rho, C_g, \Delta N)$ is irrelevant to the glucose concentration information and typically changes irregularly, which is a main cause for difficulty of directly extracting the glucose concentration variation from $\Delta I(\rho, \Delta C_g, \Delta N)$.

The diffuse reflection light intensity at the floating reference position $\rho_R$ is insensitive or irrelevant to the glucose concentration variation, i.e., $$\Delta I_S(\rho_R, \Delta C_g, N)=0 \quad (48).$$

Thus, the light intensity variation at the floating reference position is caused by only the background interference, i.e., $$\Delta I(\rho_R, \Delta C_g, \Delta N) = \Delta I_N(\rho_R, C_g, \Delta N) \quad (49).$$

Similarly, respective diffuse reflection light intensity variations at inner-side and outer-side positions with respect to the floating reference position are:

$$\Delta I(\rho_I, \Delta C_g, \Delta N) = \Delta I_S(\rho_I, \Delta C_g, N) + \Delta I_N(\rho_I, C_g, \Delta N) \quad (50); \text{ and}$$

$$\Delta I(\rho_O, \Delta C_g, \Delta N) = \Delta I_S(\rho_O, \Delta C_g, N) + \Delta I_N(\rho_O, C_g, \Delta N) \quad (51).$$

As the background interference variation $\Delta I_N(\rho_R, C_g, \Delta N)$ at the floating reference position $\rho_R$ has a fixed inherent relationship with the background interference variation at the measurement position, there is:

$$\Delta I_N(\rho_I, C_g, \Delta N) = \eta_1 \Delta I_N(\rho_R, C_g, \Delta N) \quad (52); \text{ and}$$

$$\Delta I_N(\rho_O, C_g, \Delta N) = \eta_2 \Delta I_N(\rho_R, C_g, \Delta N) \quad (53).$$

Here, $\eta_1$ and $\eta_2$ are proportional coefficients. It should be noted that when different radial positions or measurement radius are used for the measurement positions, corresponding proportional relationships are also different. That is, proper weight coefficients should be used. In actual measurements, the weight coefficient can be obtained by repeated measurements while keeping the glucose concentration constant. An effective glucose signal expression may be obtain by differential operation on equations (49)-(53):

$$\Delta I_{I-R}(\Delta C_g) = \Delta I(\rho_I, \Delta C_g, \Delta N) - \eta_1 \Delta I(\rho_R, \Delta C_g, \Delta N) \quad (54); \text{ and}$$

$$\Delta I_{O-R}(\Delta C_g) = \Delta I(\rho_O, \Delta C_g, \Delta N) - \eta_2 \Delta I(\rho_R, \Delta C_g, \Delta N) \quad (55).$$

According to equation (54), chemical metrology modeling analysis may be performed using information from the inner-side position with respect to the floating reference position and the floating reference position. According to equation (55), chemical metrology modeling analysis may be performed using information from the outer-side position with respect to the floating reference position and the floating reference position. Equation (52) may be divided by equation (53) if the information from the floating reference position is not used:

$$\Delta I_N(\rho_I, C_g, \Delta N) = \frac{\eta_1}{\eta_2} \Delta I_N(\rho_O, C_g, \Delta N). \quad (56)$$

Thus, if signals from the inner-side and outer-side positions with respect to the floating reference position are used, an effective measurement signal $\Delta I_{I-O}(\Delta C_g)$ is:

$$\Delta I_{I-O}(\Delta C_g) = \frac{\eta_1}{\eta_2} \Delta I(\rho_O, \Delta C_g, \Delta N) - \Delta I(\rho_I, \Delta C_g, \Delta N) = \quad (57)$$

$$\frac{\eta_1}{\eta_2} \Delta I_S(\rho_O, \Delta C_g, N) - \Delta I_S(\rho_I, \Delta C_g, N).$$

The glucose information obtained by differential process based on the diffuse reflection signal at the floating reference position has a higher specificity than that obtained from directly measured variation in intensity of the diffuse reflection light, because the background interference in the actual measurement are reduced effectively.

In this embodiment, the light source emission drift is simulated by changing the number of the incident photons by ±20%. As can be seen from FIG. 13, at a wavelength of 1300 nm, the floating reference position of glucose is near 1.3 mm. Thus, a radial position at 0.7-0.9 mm may be selected as the inner-side measurement position with respect to the floating reference position, e.g., region A in FIG. 14, and spectrum $I(\rho_I)$ is measured at this position. A radial position at 1.3 mm may be selected as the floating reference position, e.g., region B in FIG. 14, and spectrum $I(\rho_R)$ is measured at this position. A radial position at 1.8-2.0 mm may be selected as the outer-side measurement position with respect to the floating reference position, e.g., region C in FIG. 14, and spectrum $I(\rho_O)$ is measured at this position.

When the solution contains no glucose, i.e., only a noise signal caused by the light source emission drift exists, corresponding noise signals will be generated at the same measurement position due to the light source emission drift. Table 1 shows numbers of diffuse reflection photons at different measurement positions obtained from Monte Carlo simulation for different numbers of incident photons. Table 2 shows variations in number of the diffuse reflection photons at respective measurement positions when the number of the incident photons changes by ±20% from $10^9$. Also, Table 2-1 shows relative variations in number of the diffuse reflection photons. It can be seen that the relative variations in number of the diffuse reflection photons are substantially the same at the three measurement positions. Thus, a ratio $\xi$ between the relative variations in number of the diffuse reflection photons at any two of these positions is about 1.

TABLE 1

| Number of Incident Photons $I_0$ | Inner Side $I_N(\rho_I, \Delta N)$ | Reference Position $I_N(\rho_R, \Delta N)$ | Outer Side $I_N(\rho_O, \Delta N)$ |
| --- | --- | --- | --- |
| $0.8*10^9$ | 27039295 | 3846373 | 4085841 |
| $0.9*10^9$ | 30406696 | 4324129 | 4597030 |
| $10^9$ | 33791785 | 4808563 | 5106881 |
| $1.1*10^9$ | 37164699 | 5284565 | 5618261 |
| $1.2*10^9$ | 40541366 | 5767701 | 6127300 |

TABLE 2

| Light Source Emission Drift | Inner Side $\Delta I_N(\rho_I, \Delta N)$ | Reference Position $\Delta I_N(\rho_R, \Delta N)$ | Outer Side $\Delta I_N(\rho_O, \Delta N)$ |
| --- | --- | --- | --- |
| −20% | −6752490 | −962190 | −1021041 |
| −10% | −3385089 | −484434 | −509851 |
| 10% | 3372914 | 476001.5 | 511379.8 |
| 20% | 6749581 | 959138.1 | 1020419 |

TABLE 2-1

| Light Source Emission Drift | Inner Side $\Delta I_N (\rho_I, \Delta N)/ I_N (\rho_I, \Delta N)$ | Reference Position $\Delta I_N (\rho_R, \Delta N)/ I_N (\rho_R, \Delta N)$ | Outer Side $\Delta I_N (\rho_O, \Delta N)/ I_N (\rho_O, \Delta N)$ |
|---|---|---|---|
| −20% | −24.97% | −25% | −24.98% |
| −10% | −11.13% | −11.2% | −11.09% |
| 10% | 9.07% | 9.007% | 9.1% |
| 20% | 16.65% | 16.63% | 16.65% |

As the glucose concentration is constant, the variations of the measured signals are completely caused by the light source emission drift, and thus can be considered as the noise signal. Ratios between respective noise interferences at different measurement positions may then be calculated as shown in Table 3.

TABLE 3

| Light Source Emission Drift | $\dfrac{\Delta I_N (\rho_I, \Delta N)}{\Delta I_N (\rho_R, \Delta N)}$ | $\dfrac{\Delta I_N (\rho_O, \Delta N)}{\Delta I_N (\rho_R, \Delta N)}$ | $\dfrac{\Delta I_N (\rho_I, \Delta N)}{\Delta I_N (\rho_O, \Delta N)}$ |
|---|---|---|---|
| −20% | 7.017834 | 1.061163 | 6.613341 |
| −10% | 6.987722 | 1.052468 | 6.639366 |
| 10% | 7.085932 | 1.074324 | 6.595712 |
| 20% | 7.037131 | 1.063891 | 6.614521 |

Any of the ratios between the respective noise interferences at the different measurement positions as shown in Table 3 may also be obtained directly as follows. As ξ is determined as 1, η can be obtained directly using equation (S-3), as shown in Table 3-1.

TABLE 3-1

| Light Source Emission Drift | $\dfrac{I_N (\rho_I, \Delta N)}{I_N (\rho_R, \Delta N)}$ | $\dfrac{I_N (\rho_O, \Delta N)}{I_N (\rho_R, \Delta N)}$ | $\dfrac{I_N (\rho_I, \Delta N)}{I_N (\rho_O, \Delta N)}$ |
|---|---|---|---|
| 0% | 7.027 | 1.062 | 6.6169 |

Comparison between Table 3 and Table 3-1 shows that the actually obtained η is substantially the same as that estimated by equation (S-3).

As can be seen from Table 3 and Table 3-1, when the glucose concentration does not change while the light source emission drifts,
the variation of the signal at the inner-side measurement position with respect to the floating reference position $\Delta I_N(\rho_I,\Delta C_g,\Delta N)$ is about 7.0 times of the variation of the signal at the floating reference position $\Delta I_N(\rho_R,\Delta C_g,\Delta N)$, i.e., $\Delta I_N(\rho_I,\Delta C_g,\Delta N)=7.0\Delta I_N(\rho_R,\Delta C_g,\Delta N)$;
the variation of the signal at the outer-side measurement position with respect to the floating reference position $\Delta I_N(\rho_O,\Delta C_g,\Delta N)$ is about 1.06 times of the variation of the signal at the floating reference position $\Delta I_N(\rho_R,\Delta C_g,\Delta N)$, i.e., $\Delta I_N(\rho_O,\Delta C_g,\Delta N)=1.06\Delta I_N(\rho_R,\Delta C_g,\Delta N)$; and
the variation of the signal at the inner-side measurement position with respect to the floating reference position $\Delta I_N(\rho_I,\Delta C_g,\Delta N)$ is about 6.6 times of the variation of the signal at the outer-side measurement position with respect to the floating reference position $\Delta I_N(\rho_O,\Delta C_g,\Delta N)$, i.e., $\Delta I_N(\rho_I,\Delta C_g,\Delta N)=6.6\Delta I_N(\rho_O,\Delta C_g,\Delta N)$.

When the glucose concentration and the light source both change, as the light intensity variation at the floating reference position is irrelevant to variation of the glucose concentration, the intensity variation at this position is only caused by the light source emission drift. According to equations (54) and (55), useful signals at the inner-side and outer-side positions with respect to the floating reference position caused by the glucose concentration variation are:

$$\Delta I_{I-R}(\Delta C_g)=\Delta I(\rho_I,\Delta C_g,\Delta N)-7.0\Delta I(\rho_R,\Delta C_g,\Delta N) \quad (58); \text{ and}$$

$$\Delta I_{O-R}(\Delta C_g)=\Delta I(\rho_O,\Delta C_g,\Delta N)-1.06\Delta I(\rho_R,\Delta C_g,\Delta N) \quad (59)$$

Table 4 shows 6 groups of glucose concentrations and numbers of incident photons for deriving diffuse reflection spectra.

TABLE 4

| | Glucose Concentration (mM) | Incident Photon Number |
|---|---|---|
| 1 | 0 | $0.8*10^9$ |
| 2 | 20 | $1.2*10^9$ |
| 3 | 40 | $1.1*10^9$ |
| 4 | 60 | $0.8*10^9$ |
| 5 | 80 | $0.9*10^9$ |
| 6 | 100 | $1*10^9$ |

Figure 15:
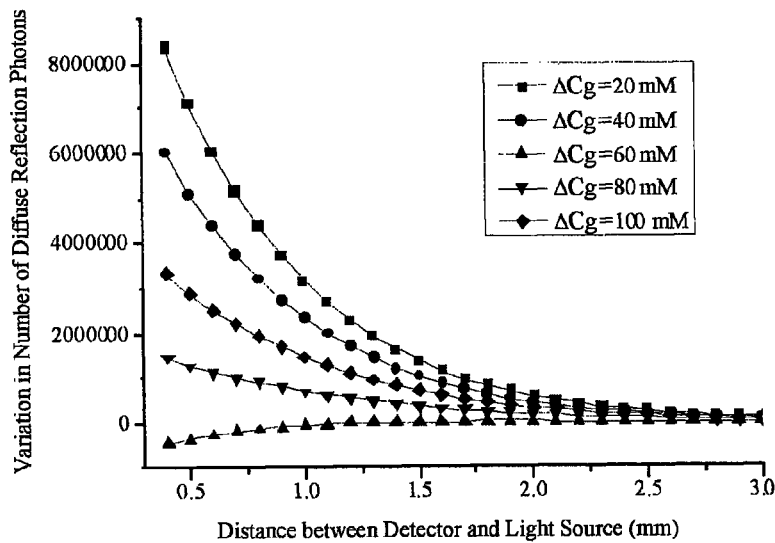
FIG. 15 is a graph showing variations in number of diffuse reflection photons at different radial positions from a light source before light source emission drift correction.

FIG. 15 shows variations in number of diffuse reflection photons at different radial positions from the light source when the glucose concentration variation is 20, 40, 60, 80, and 100 mM, before the light source emission drift is corrected. It can be seen that measured diffuse reflection light intensity curves do not increase or decrease regularly with the glucose concentration. Thus, signal variations caused by the light source emission drift overwhelm characteristic signals caused by the glucose concentration variations.

Similarly, the inner-side measurement position with respect to the floating reference position is 0.7-0.9 mm, the reference position is 1.3 mm, and the outer-side measurement position is 1.8-2 mm. Table 5 shows variations in number of diffuse reflection photons at respective measurement positions when the glucose concentration changes, before the light source emission drift is corrected.

TABLE 5

| Glucose Concentration Variation (mM) | Inner Side $\Delta I (\rho_I, \Delta C_g, \Delta N)$ | Reference Position $\Delta I (\rho_R, \Delta C_g, \Delta N)$ | Outer Side $\Delta I (\rho_O, \Delta C_g, \Delta N)$ |
|---|---|---|---|
| 20 | 13288959 | 1921647 | 2081711 |
| 40 | 9722511 | 1440496 | 1600484 |
| 60 | −452879 | −2893.97 | 76361.63 |
| 80 | 2703350 | 476415.3 | 622562.5 |
| 100 | 5820571 | 954645.7 | 1175567 |

Table 6 shows variations in number of diffuse reflection photons at the inner-side and outer-side positions with respect to the floating reference position, which are corrected for the light source emission drift by equations (58) and (59) using information of the floating reference position.

TABLE 6

| Glucose Concentration Variation (mM) | Inner Side $\Delta I_S (r_I, \Delta C_g)$ | Outer Side $\Delta I_S (r_O, \Delta C_g)$ |
|---|---|---|
| 20 | −162567 | 44765.59 |
| 40 | −360961 | 73558.11 |
| 60 | −432622 | 79429.25 |

TABLE 6-continued

| Glucose Concentration Variation (mM) | Inner Side $\Delta I_S$ ($r_I$, $\Delta C_g$) | Outer Side $\Delta I_S$ ($r_O$, $\Delta C_g$) |
|---|---|---|
| 80 | −631557 | 117562.3 |
| 100 | −861950 | 163643 |

Figure 16:
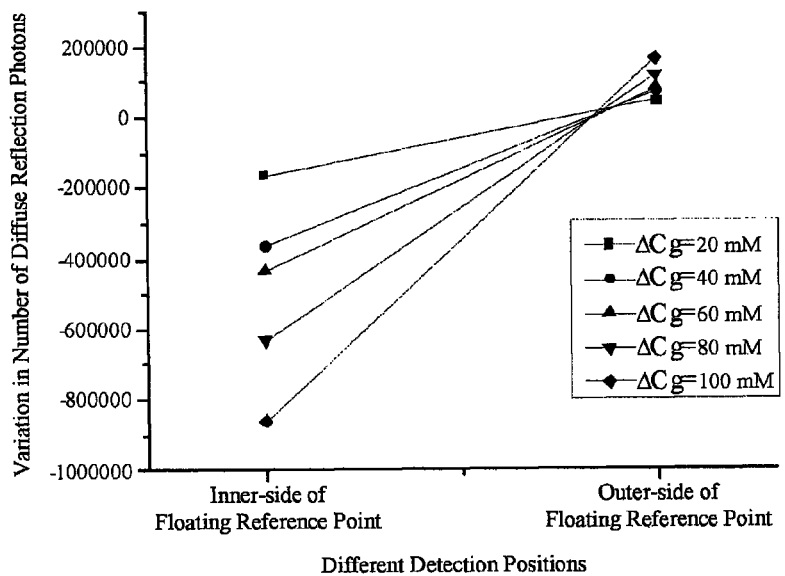
FIG. 16 is a graph showing variations in number of diffuse reflection photons at different radial positions after light source emission drift correction.

As can be seen from FIG. 16, the number of the diffuse reflection photons at the inner-side of the floating reference position decreases with increase of the glucose concentration variation, and a variation sign thereof is negative. The number of the diffuse reflection photons at the outer-side of the floating reference position increases with increase of the glucose concentration variation, and a variation sign thereof is positive. This removes the influence of the light source emission drift effectively.

If the measurement information at the floating reference position is not used, as can be seen from the foregoing calculations, the variation of the signal at the inner-side measurement position with respect to the floating reference position $\Delta I_N(\rho_I, \Delta C_g, \Delta N)$ is about 6.6 times of the variation of the signal at the floating reference position $\Delta I_N(\rho_O, \Delta C_g, \Delta N)$, i.e., $\Delta I_N(\mu_I, \Delta C_g, \Delta N) = 6.6 \Delta I_N(\rho_O, \Delta C_g, \Delta N)$. The measurement signals at the inner-side and outer-side measurement positions with respect to the floating reference position are subjected to weighted differential operation according to equation (57), i.e., $$\Delta I_{I-O}(\Delta C_g) = 6.6\Delta I(\rho_O, \Delta C_g, \Delta N) - \Delta I(\rho_I, \Delta C_g, \Delta N) \quad (60)$$

The resultant signal is a weighted sum of the effective signals at the inner-side and outer-side positions with respect to the floating reference position, which completely removes the noise caused by the light source emission drift.

Table 7 shows $\Delta I_{I-O}(\Delta C_g)$ for different glucose concentration variations corrected for both the glucose concentration variation and the light source emission drift by equation (60) using the measurement signals at the inner-side and outer-side positions with respect to the floating reference position without using the floating reference position information. It shows that, by the weighted differential processing of the measurement signals at the inner-side and outer-side positions with respect to the floating reference position, the effective signal $\Delta I_{I-O}(\Delta C_g)$ increases with increase of the glucose concentration variation. This effectively removes the common-mode interference caused by the light source emission drift.

TABLE 7

| Glucose Concentration Variation (mM) | $\Delta I_S$ ($\Delta C_g$) |
|---|---|
| 20 | 450333.3 |
| 40 | 840682.6 |
| 60 | 956866.2 |
| 80 | 1405562 |
| 100 | 1938175 |

Spectrum signals measured at other different wavelengths may be corrected for the light source emission drift in a similar way. A Partial Least Square model may be established using effective signals $\Delta I_S(\lambda_i)$ at respective wavelengths obtained by weighted differential processing in combination with a series of corresponding reference concentration parameters. Prediction of spectra at unknown concentrations may then be performed.

According to another example, a case where temperature of the medium to be detected changes may be analyzed by Monte Carlo simulation using received signals from the inner-side and outer-side measurement positions with respect to the floating reference position.

For 2% intralipid solution, the floating reference position does not exist when the wavelength becomes greater than 1400 nm. That is, the theory of the floating reference position measurement method does not apply for wavelengths greater than 1400 nm. Thus, using the intralipid solution at the concentration of 2%, Monte Carlo simulation is performed for a case where the diffuse reflection light varies with the glucose concentration and temperature variations at a wavelength of 1600 nm. The glucose concentration varies in a range of 0-100 mM with an interval of 20 mM. The temperature varies in a range of 32° C.-40° C. with an interval of 0.5° C. A number of incident photons is $10^{11}$. An absolute number of photons obtained by diffuse reflection from the sample constitutes exit light. Respective variations in absorption coefficient and scattering coefficient when the temperature changes are:

$$\Delta\mu_a(1600 \text{ nm}) = -0.0037T + 0.1081 \quad (61); \text{ and}$$

$$\Delta\mu_s = 4.7 \times 10^{-3} \text{ C.}^{-1} \times \Delta T \times \mu_s \quad (62).$$

Figure 25:
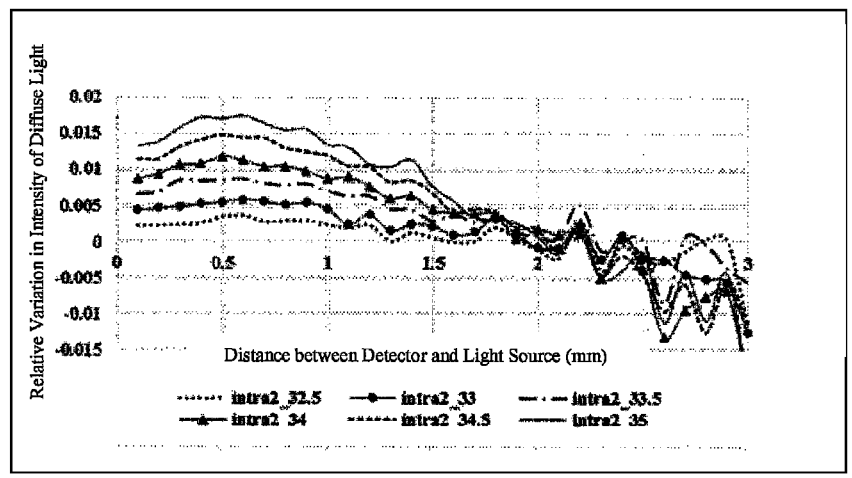
FIG. 25 is a schematic view showing existence of a single temperature function line and a temperature reference point.

FIG. 25 shows relative variations of the diffuse reflection light caused by the temperature variation with respect to the exit light at 32° C. when only the temperature changes for a wavelength of 1600 nm.

It can be seen that there is a position insensitive to the temperature variation when a distance between a light source and a detector is about 2 mm, which may be called "temperature reference position". In a certain range far away from the light source, relative variations in intensity at different positions are substantially linear. It should be noted that the intensity of the exit light decreases significantly at positions too far away from the light source. Consequently, the influence of the noise increases and thus the measurement will be significantly affected. In a case where the noise is relatively small, the value of ξ may be estimated for two fixed measurement positions according to FIG. 25. The value of η may then be obtained directly using equation (S-3).

The below calculation uses the noise value actually caused by the temperature variation to obtain an accurate value of η.

Figure 17:
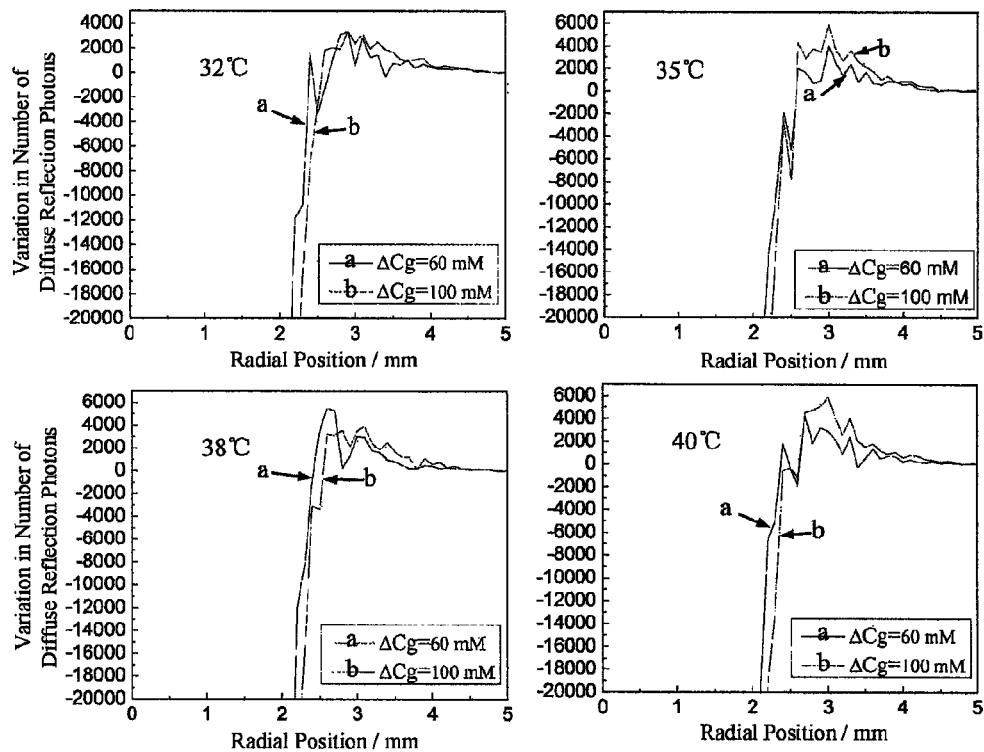
FIG. 17 is a schematic view showing variations in number of diffuse reflection photons caused by variation in glucose concentration at respective radial positions at different temperatures.

FIG. 17 shows a distribution diagram of respective variations of diffuse reflection light at different radial positions for glucose concentration variations of 60 mM and 100 mM at 32° C., 35° C., 38° C., and 40° C. As can be seen from the figure, at this wavelength, there is no radial position where sensitivity of the light intensity to the glucose concentration variation is always substantially zero, i.e., there is no floating reference position. However, at any temperature, there is always a radial position range where the diffuse reflection light intensity variation is negative with respect to the glucose concentration variation. Moreover, in this region, the diffuse reflection light variation has a higher absolute value and stability. Thus, two radial positions in this range may be selected as the measurement positions to remove the common-mode interference noise even if the floating reference position does not exist.

Here, a radial position at 0.6-1 mm is selected as measurement position 1 and a radial position at 1-2 mm is selected as measurement position 2. When the solution does not contain glucose, that is, when there is only the temperature variation, a noise signal will be caused by the temperature variation at the respective radial positions. Respective numbers of diffuse reflection photons may be obtained for the respective radial positions at different temperatures by Monte Carlo simulation. Table 8 shows respective variations in number of the diffuse reflection photons detected at the two measurement positions when the temperature changes from 32° C. to 40° C. with 36° C. as a reference, i.e., changes ±4° C. with respect to 36° C.

TABLE 8

| Temperature Variation/° C. | Measurement Position 1 $\Delta I_N(\rho_1, C_g, \Delta T)$ | Measurement Position 2 $\Delta I_N(\rho_2, C_g, \Delta T)$ | $\dfrac{\Delta I_N(\rho_2, C_g, \Delta T)}{\Delta I_N(\rho_1, C_g, \Delta T)}$ |
|---|---|---|---|
| −4 | 11073518 | 1947453 | 0.175866 |
| −3 | 8264964 | 1595398 | 0.193031 |
| −2 | 5700683 | 970479.7 | 0.170239 |
| −1 | 2782297 | 475523.5 | 0.17091 |
| 1 | −2751821 | −473829 | 0.172187 |
| 2 | −5684499 | −950272 | 0.167169 |
| 3 | −8281461 | −1422787 | 0.171804 |
| 4 | −1.10E + 07 | −1933606 | 0.175782 |

As the glucose concentration is constant, the measured signal variation is caused completely by the temperature variation. Thus, it can be considered that the measured signal variation is the noise signal. Accordingly, a ratio between noise interferences at two measurement positions may be calculated. A ratio between a variation in number of diffuse reflection photons at measurement position 2 and that at measurement position 1 is about 0.17, i.e., $$\Delta I_N(\rho_2, C_g, \Delta T) = 0.17 \Delta I_N(\rho_1, C_g, \Delta T) \qquad (63)$$

Thus, when both the glucose concentration and the temperature change, differential operation is performed on diffuse reflection light variations at $\rho_1$ and $\rho_2$ according to equation (63) to obtain an effective signal caused by the glucose concentration variation, from which the common-mode interference caused by the temperature is reduced:

$$\Delta I_{2-1}(\Delta C_g) = \Delta I(\rho_2, \Delta C_g, \Delta T) - 0.17 \Delta I(\rho_1, \Delta C_g, \Delta T) \qquad (64)$$

Consider diffuse reflection light at different glucose concentrations for six randomly-selected groups of temperatures. A correlation coefficient between the glucose concentration and the temperature is −0.01918, and thus the glucose concentration and the temperature can be considered to be uncorrelated. Based on this, a situation where the temperature drifts irregularly while the glucose concentration varies in actual measurements is emulated. Table 9 shows glucose concentrations and corresponding temperatures for the simulation.

TABLE 9

| | Glucose Concentration/mM | Temperature/° C. |
|---|---|---|
| 1 | 0 | 35 |
| 2 | 20 | 33 |
| 3 | 40 | 39 |
| 4 | 60 | 34 |
| 5 | 80 | 38.5 |
| 6 | 100 | 32.5 |

Figure 18:
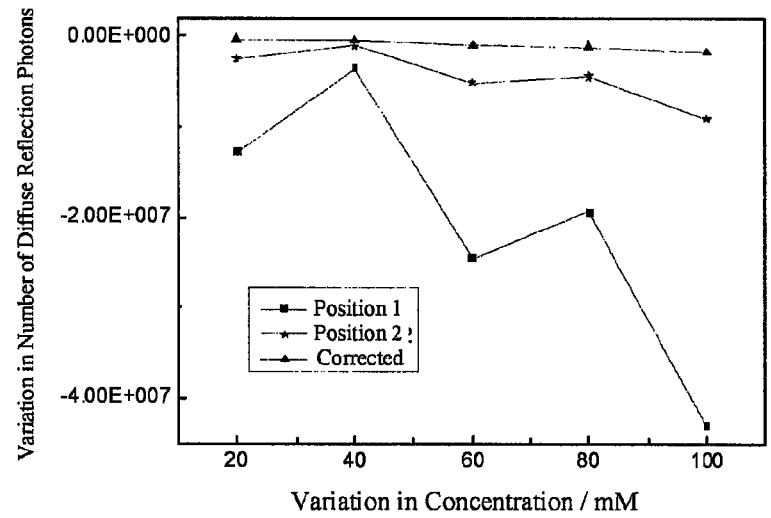
FIG. 18 is a graph showing variations in number of diffuse reflection photons with respect to concentration before and after light source emission drift correction.

Taking the first group of data as an initial state of measurement, FIG. 18 shows variations in number of diffuse reflection photons before correction of the interference signal caused by the temperature variation at same two measurement positions when the glucose concentration variation is 20, 40, 60, 80, and 100 mM, respectively. In this figure, the measured variation in intensity of the diffuse reflection light does not increase or decrease regularly with the glucose concentration variation. That is, the variation signal caused by the temperature variation overwhelms the characteristic signal caused by the glucose concentration variation.

FIG. 18 also shows variations in number of the diffuse reflection photons at the two measurement positions after the correction for the temperature variation according to equation (64). As can be seen from the figure, although the absolute value of the resultant signal which is corrected based on a weighted sum of the signals at the two measurement positions is smaller than that of the signals at the two measurement positions before the correction, the absolute value increases regularly with the glucose concentration variation, which indicates that the common-mode interference caused by the temperature drift is removed effectively.

According to another example, light source emission drift is analyzed for 3% intralipid solution using an SLD light source based multi-loop fiber measurement system.

Experiments show that for the 3% intralipid solution, the floating reference position of the glucose at a wavelength of 1219 nm is at about 3.0-3.2 mm. Thus, this position is selected as a loop for detecting signals at the floating reference position in the multi-loop fiber probe. FIG. 10(a) schematically shows a structure of the multi-loop fiber probe with a radial position of 0.24-0.96 mm as a loop for detecting signals at an inner-side measurement position and a radial position of 3.2-4.1 mm as a loop for detecting signals at an outer-side measurement position.

In the experiment, power of the SLD is changed randomly to emulate irregular drift of the light source. Diffuse reflection light intensities at three radial positions at different times are measured for a wavelength of 1219 nm. Taking a first measured value as an initial measurement state, the diffuse reflection light variation when the light source emission drifts may be obtained by differential operation on the measured intensity at that time and that at the initial state. Thus, ratios may be calculated between the diffuse reflection light signal variations at the three measurement positions caused by the light source emission drift. The calculation result shows that the diffuse reflection light signal variation caused by the light source emission drift at the outer-side measurement position with respect to the floating reference position is about 0.84 times that at the floating reference position, the diffuse reflection light signal variation at the floating reference position is about 0.7 times that at the inner-side measurement position with respect to the floating reference position, and the diffuse reflection light signal variation caused by the light source emission drift at the outer-side measurement position with respect to the floating reference position is about 0.58 times that at the inner-side measurement position with respect to the floating reference position. These may be used as differential ratio coefficients for signal correction when both the light source state and the glucose concentration vary, i.e., $$\Delta I_N(\rho_O, C_g, \Delta N) = 0.84 \Delta I_N(\rho_R, C_g, \Delta N) \qquad (65)$$

$$\Delta I_N(\rho_R, C_g, \Delta N) = 0.7 \Delta I_N(\rho_I, C_g, \Delta N) \qquad (66)$$

$$\Delta I_N(\rho_O, C_g, \Delta N) = 0.58 \Delta I_N(\rho_I, C_g, \Delta N) \qquad (67)$$

Figure 19:
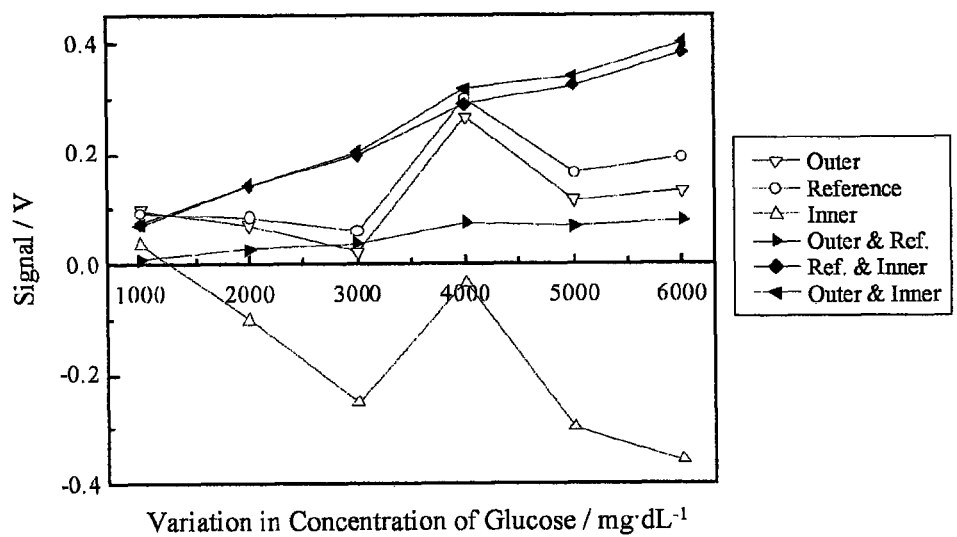
FIG. 19 is a schematic view showing a comparison between signals before and after correction with 0 mg/dL glucose as an initial state.

Next, six samples are prepared having the glucose concentration in a range of 1000-6000 mg/dL with an interval of 1000 mg/dL using 3% intralipid solution as mother solution. The six glucose intralipid solution samples are measured randomly while the SLD power is changed randomly to emulate irregular drift of the light source. Diffuse reflection light intensities at three radial positions are measured at different times and the diffuse reflection light intensities of the solution samples and that of the initial state are subjected to differential operation, to obtain diffuse reflection light variations at the three measurement positions when both the light source emission drift and the glucose concentration variations exist. FIG. 19 shows the calculation result. As can be seen from the result, the light source emission drift has a significant influence on the measurement of the glucose concentration. The measurement signals at the three positions are no longer linear with respect to the glucose concentration variation due to the randomness of the light source emission drift. In other words, the diffuse reflection light intensity variation caused by the light source emission drift overwhelms effective information related to the glucose concentration variation. Therefore, it is necessary to correct the measured light intensity.

FIG. 19 shows correction results of the diffuse reflection light intensity signals caused by the glucose concentration variation and the light source emission drift collectively by equations (54), (55), and (57) using the proportional relations shown in equations (65), (66), and (67). As can be seen from the results, the light intensity signals at two arbitrary positions corrected by the weighted differential processing have an obvious linear relation to the glucose concentration variation. The effect of the light source emission drift on the glucose concentration measurement has been reduced or removed, whereby enabling effective extraction of the glucose concentration variation. Also as can be seen from the results, the effective signal value corrected using the measured signals from the inner loop and the reference loop or those from the outer loop and the inner loop is substantially greater than the effective signal value corrected using the measured signals from the outer loop and the reference loop. This is because the diffuse reflection light intensity attenuates exponentially as the radial distance from the light source increases. Correction effect using the inner loop and the outer loop is comparable to that using the inner loop and the reference loop. However, when the inner loop and the outer loop are used, the measured signal from the reference loop is not used, and thus the influence of the light wavelength, the state of the subject to be detected, or the like on the floating reference position can be avoided. This may effectively enhance the universality of the signal correction method.

Figure 20:
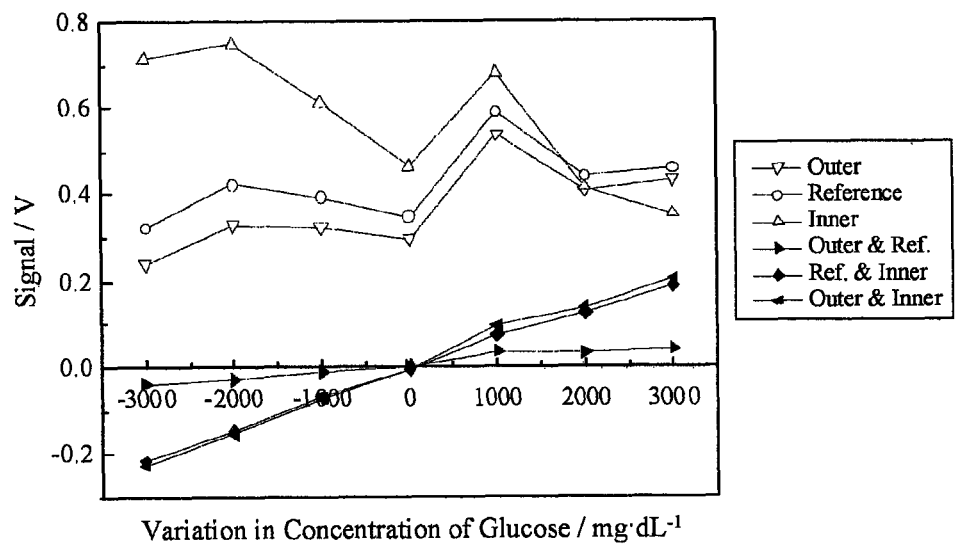
FIG. 20 is a schematic view showing a comparison between signals before and after correction with 3000 mg/dL glucose as an initial state.
Figure 21:
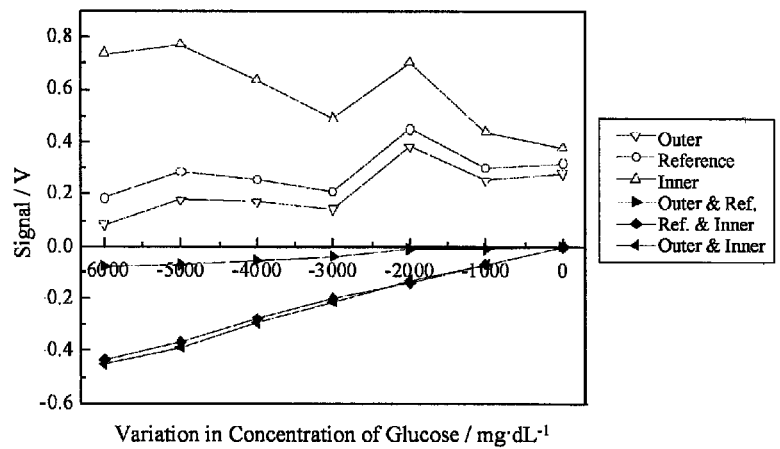
FIG. 21 is a schematic view showing a comparison between signals before and after correction with 6000 mg/dL glucose as an initial state.

In the foregoing analysis, the 3% pure intralipid solution is used to obtain the proportional coefficients with respect to the light source emission drift, and also used as the initial measurement state for subsequent signal processing. Similarly, corresponding proportional coefficients may be calculated for a glucose solution sample at a different concentration with respect to random light source emission drift by similar steps, and then the sample at the concentration can be used as an initial measurement state for subsequent signal processing. FIGS. 20 and 21 show signal correction results using samples at glucose concentrations of 3000 and 6000 mg/dL, respectively, to obtain proportional coefficients and also as the initial measurement state. As can be seen from the figures, the common-mode interference caused by the light source emission drift can also be reduced or removed by using the glucose solution at different concentrations as the initial state. Also, the correction effect using the signals at the inner and outer measurement positions or the signals at the inner measurement position and floating reference position is better than that using the signals at the outer measurement position and floating reference position. This is the same as the situation where the pure intralipid solution is used as the initial sample. Also it should be noted that the corrected result is always a glucose concentration variation compared to the glucose concentration at the initial state. Thus, the measured glucose concentration should be a sum of the variation and the glucose concentration at the initial state.

Figure 22:
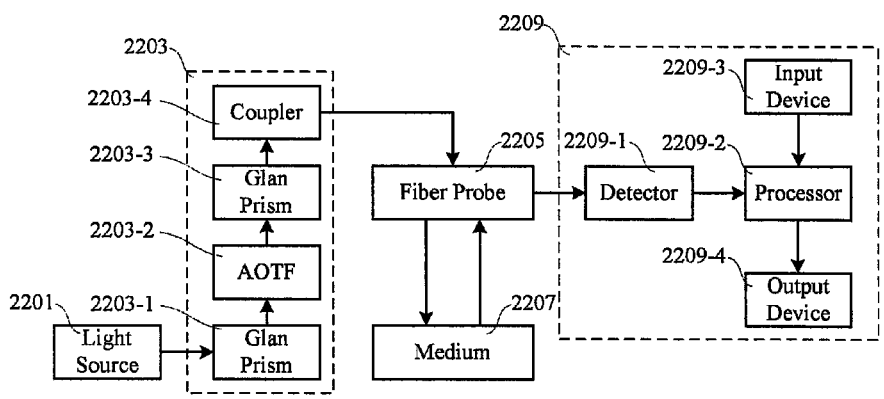
FIG. 22 is a schematic view showing a configuration example of a measurement system according to an embodiment of the present disclosure.

FIG. 22 shows a configuration example of a measurement system according to an embodiment of the present disclosure.

As shown in FIG. 22, the measurement system may comprise a light source 2201, a coupling system 2203 for coupling light from the light source 2201 to fibers, a fiber probe 2205, and a processing apparatus 2209.

The light source 2201 may include any suitable light source capable of emitting light at a desired wavelength. For example, a halogen lamp may be used as a continuous light source in the near-infrared range. Alternatively, the light source 2201 may comprise a supercontinuum pulse laser source.

The coupling system 2203 may include a Glan prism 2203-1 configured to transform the light from the light source 2201 to linearly polarized light, a Acousto optic Tunable Filter (AOTF) 2203-2 configured to split (diffract) the linearly polarized light from the Glan prism 2203-1 to order +1 or −1 light having a polarization state perpendicular to that of order 0 light, a Glan prism 2203-3 arranged perpendicular to the Glan prism 2203-1 and configured to eliminate the order 0 light, and a coupler 2203-4 configured to couple the order +1 or −1 light from the Glan prism 2203-3 to subsequent devices.

Although FIG. 22 shows a specific example of the coupling system, the present disclosure is not limited thereto. Those skilled in the art know various coupling system capable of coupling the light from the light source into the fiber system.

The fiber probe 2205 may include, e.g. the structure described with reference to FIG. 10. Specifically, the coupling system 2203 may couple the light from the light source into the incident fiber bundle (e.g., 1001 in FIG. 10) of the fiber probe 2205. The incident fiber bundle may direct the light to the medium to be detected 2207. Thus, the detection fiber bundles (e.g., two or more of 1003, 1005, and 1007 in FIG. 10) may direct the diffuse reflection light from the medium to be detected 2007 into the processing apparatus 2209.

The processing apparatus 2209 may comprise a detector 2209-1 (e.g., a photoelectric detector) configured to detect optical signals from the fiber probe and convert them to electric signals for further processing. Due to the configuration of the fiber probe, the detector 2209-1 may detect spectral data at various radial positions (e.g., the inner position with respect to the floating reference position, the floating reference position, and the outer position with respect to the floating reference position).

The processing apparatus 2209 may further comprise a processor 2209-2. The processor 2209-2 may be configured to perform differential processing on the spectrum measured by the detector 2209-1 as described above. Specifically, the processor 2209-2 may select two radial positions where the variation rates of the diffuse reflection light intensity have different signs with respect to the concentration variation of the particular component in the medium to be detected, and perform weighted differential processing on the spectral data at these two radial positions.

The processor 2209-2 may comprise various forms of computing devices, such as, general computer, Application Specific Integrated Circuit (ASIC), Field Programmable Gate Array (FPGA), or the like. The processor 2209-2 may work in the respective flows as described above by loading programs or code segments stored in storage, to perform the differential processing of the spectral data, model establishment, and concentration prediction.

The processing apparatus may further comprise an input device 2209-3, such as, mouse, keyboard, or the like, for inputting user commands, data, or the like, and an output device 2209-4, such as display, for outputting process results of the processor 2209-2 (for example, prediction results, or the like). The input device 2209-3 and the output device 2209-4 may be implemented in combination by a touch screen.

The technology disclosed herein may also be embodied by a program comprising algorithm executable in a data processing device, or may be stored in and thus provided as a non-transitory computer readable medium.

The technology disclosed herein may also be embodied by computer readable codes on a computer readable medium. The computer readable medium may comprise a computer readable recording medium and a computer readable transmission medium. The computer readable recording medium refers to any storage device capable of storing data as a program which can be read by a computer system later. Examples of the computer readable recording medium include Read-Only Memory (ROM), Random Access Memory (RAM), Compact Disk ROM (CD-ROM), magnetic tape, floppy disk, and optical data storage. The computer readable recording medium may be distributed over a networked computer system, so that the computer readable codes are saved and executed in a distributed manner. The computer readable transmission medium can be conveyed by carriers or signals (by wired or wireless data transmission via Internet, for example). Further, functional programs, codes, and code segments to implement the technology disclosed herein can be readily interpreted by programmers in the art to which the present inventive concept belongs.

Various features of the present disclosure are described in the respective embodiments. However, this does not necessarily mean that those features cannot be used in combination to advantage.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A method of predicting a change in concentration of a particular component in a medium to be detected with respect to a reference based on spectral data, comprising the steps of:
   illuminating the medium with light;
   selecting a first radial position and a second radial position based on a reference position, wherein each of the first radial position, the second radial position, and the reference position is a radial position on a pathway of the light passing through the medium, and wherein the reference position indicates a radial position where intensity of diffuse reflection light and/or diffuse transmission light varies with a variation in concentration of the particular component at a variation rate with a substantially minimal absolute value,
   obtaining a first spectral data for the medium at the first radial position and a second spectral data for the medium at the second radial position caused by the concentration change with respect to the reference;
   calculating a differential between the first spectral data and the second spectral data; and
   predicting the concentration change of the particular component based on the calculated differential.

2. The method of claim 1,
   wherein intensity of diffuse reflection light and diffuse transmission light, which is detected at the first radial position, varies at a first variation rate with a variation in concentration of the particular component in the medium,
   wherein intensity of diffuse reflection light and/or diffuse transmission light, which is detected at the second radial position, varies at a second variation rate with the concentration variation of the particular component in the medium, and
   wherein the first radial position and the second radial position are selected in such a way that the first variation rate and the second variation rate have different signs.

3. The method of claim 2, wherein
the first variation rate has a positive sign, and the second variation rate has a negative sign, or the first variation rate has a positive sign or a negative sign and the second variation rate is substantially zero.

4. The method of claim 1, wherein the variation rate at the reference position is substantially zero.

5. The method of claim 1, wherein the step of selecting the first radial position and the second radial position comprises:
   (a) selecting a position closer to a light source than the reference position as the first radial position, and a position farther away from the light source than the reference position as the second radial position, or
   (b) selecting the reference position as the first radial position, and a position closer to a light source than the reference position as the second radial position, or
   (c) selecting the reference position as the first radial position, and a position farther away from the light source than the reference position as the second radial position.

6. The method of claim 5, wherein in case of (a), the method further comprises the step of:
   obtaining a third spectral data at the reference position caused by the concentration change with respect to the reference.

7. The method of claim 1, wherein the first spectral data and the second spectral data each comprise a change in light intensity measured for the medium with respect to the reference.

8. The method of claim 7, wherein the step of calculating a differential comprises:
   subtracting the light intensity change at the second radial position weighted by a factor η from the light intensity change at the first radial position,
   wherein the factor η is a ratio between a light intensity variation of diffuse reflection light and/or diffuse transmission light at the first radial position and that at the second radial position cause by a same interference factor while the concentration of the particular component keeps substantially unchanged.

9. The method of claim 8, wherein the factor η is calculated from optical parameters of the medium.

39

10. The method of claim 9, wherein the optical parameters of the medium is obtained by reverse construction of the optical parameters.

11. The method of claim 8, wherein the factor η is obtained by a plurality of measurements.

12. The method of claim 8, wherein the factor η is estimated by multiplying a ratio between the light intensity at the first radial position and the light intensity at the second radial position for the reference with a fixed coefficient.

13. The method of claim 12, wherein the fixed coefficient is estimated based on the first radial position and the second radial position.

14. The method of claim 1, wherein the first spectral data and the second spectral data each include a relative change in light intensity measured for the medium with respect to the reference.

15. The method of claim 1, wherein the predicting is performed based on a prediction model, wherein the prediction model is established by:
for each medium of a series of media, wherein the medium comprises a background or reference medium with the particular component at a respective known concentration added into the background or reference medium, wherein the reference medium comprises the background medium and the particular component at an initial concentration:
illuminating the medium with light;
obtaining a first spectral data for the medium at a first radial position caused by the concentration change with respect to the background or reference medium and a second spectral data for the medium at a second radial position caused by the concentration change with respect to the background or reference medium, wherein the first radial position and the second radial position are selected arbitrarily;
calculating a differential between the first spectral data and the second spectral data; and
establishing the prediction model based on the respective known concentrations and corresponding calculated differential.

16. The method of claim 15, wherein the method is used in non-invasive detection of blood glucose concentration.

17. The method of claim 16, wherein the applied light has a wavelength in a range of about 1.0-2.4 μm.

18. A processing apparatus, comprising:
a detector configured to detect spectral data of diffuse reflection light and/or diffuse transmission light from a medium to detect an inside particular component; and
a processor configured to:
select a first radial position and a second radial position based on a reference position, wherein each of the first radial position, the second radial position, and the reference position is a radial position on a pathway of the light passing through the medium, and the reference position indicates a radial position where intensity of diffuse reflection light and/or diffuse transmission light varies with a variation in concentration of the particular component at a variation rate with a substantially minimal absolute value;
obtain spectral data at the first radial position and the second radial position caused by a change in concentration of the particular component with respect to a reference by using the detector; and
calculate a differential between the detected spectral data at the first radial position and the second radial position.

40

19. The processing apparatus of claim 18,
wherein intensity of the diffuse reflection light and the diffuse transmission light, which is detected at the first radial position, varies at a first variation rate with a variation in concentration of the particular component in the medium,
wherein intensity of the diffuse reflection light and the diffuse transmission light, which is detected at the second radial position, varies at a second variation rate with a variation in concentration of the particular component in the medium, and
wherein the first radial position and the second radial position are selected in such a way that the first variation rate and the second variation rate have different signs.

20. A method of predicting a change in concentration of a particular component in a medium to be detected with respect to a reference based on spectral data, comprising the steps of:
illuminating the medium with light;
selecting a first radial position and a second radial position wherein each of the first radial position and the second radial position is a radial position on a pathway of the light passing through the medium, wherein intensity of diffuse reflection light and/or diffuse transmission light detected at the first radial position and the second radial position varies at a first variation rate and a second variation rate with the concentration variation of the particular component in the medium, respectively, and wherein the first radial position and the second radial position are selected in such a way that the first variation rate and the second variation rate have different signs;
obtaining a first spectral data for the medium at the first radial position and a second spectral data for the medium at the second radial position caused by the concentration change with respect to the reference;
calculating a differential between the first spectral data and the second spectral data; and
predicting the concentration change of the particular component based on the calculated differential.

21. The method of claim 20, wherein:
the first variation rate has a positive sign, and the second variation rate has a negative sign, or
the first variation rate has a positive sign or a negative sign and the second variation rate is substantially zero.

22. A processing apparatus comprising:
a detector configured to detect spectral data of diffuse reflection light and/or diffuse transmission light from a medium to detect an inside particular component; and
a processor configured to:
select a first radial position and a second radial position, wherein each of the first radial position and the second radial position is a radial position on a pathway of the light passing through the medium, wherein intensity of diffuse reflection light and/or diffuse transmission light detected at the first radial position and the second radial position varies at a first variation rate and a second variation rate with the concentration variation of the particular component in the medium, respectively, and wherein the first radial position and the second radial position are selected in such a way that the first variation rate and the second variation rate have different signs;
obtain spectral data at the first radial position and the second radial position caused by a change in concentration of the particular component with respect to a reference by using the detector; and calculate a differential between the detected spectral data at the first radial position and the second radial position.

23. The processing apparatus of claim 22, wherein
the first variation rate has a positive sign, and the second variation rate has a negative sign, or
the first variation rate has a positive sign or a negative sign and the second variation rate is substantially zero.

* * * * *